United States Patent [19]

Botsford

[11] Patent Number: 5,792,622
[45] Date of Patent: Aug. 11, 1998

[54] ASSAY FOR CHEMICALS

[75] Inventor: James L. Botsford, Las Cruces, N. Mex.

[73] Assignee: New Mexico State University Technology Transfer Corporation, N. Mex.

[21] Appl. No.: 558,898

[22] Filed: Nov. 16, 1995

[51] Int. Cl.$^6$ .................. C12Q 1/02; C12Q 1/00; C12N 1/00; G01N 33/53

[52] U.S. Cl. .................. 435/29; 435/878; 435/886; 435/830; 435/879; 435/833; 435/837; 435/849; 435/874; 435/252.8; 435/968; 435/4; 436/63; 436/172; 436/800; 436/801

[58] Field of Search .................. 435/29, 849, 255.1, 435/254.1, 254.9, 256.6, 251.1, 878, 886, 830, 879, 833, 837, 874, 252.8, 968, 4; 436/63, 172, 800, 801

[56] References Cited

U.S. PATENT DOCUMENTS

| | | | |
|---|---|---|---|
| 3,043,751 | 7/1962 | Goldman | 195/103.5 |
| 3,107,204 | 10/1963 | Brown et al. | 195/103.5 |
| 3,126,325 | 3/1964 | Poole | 195/103.5 |
| 3,197,384 | 7/1965 | Goldman | 195/103.5 |
| 3,370,175 | 2/1968 | Jordan et al. | 250/217 |
| 3,941,658 | 3/1976 | Lameris et al. | 195/103.5 |
| 4,340,671 | 7/1982 | Gibson | 435/32 |
| 4,513,280 | 4/1985 | Hannan et al. | 340/632 |
| 4,564,453 | 1/1986 | Coplot et al. | 210/614 |
| 4,929,546 | 5/1990 | Mayra-Makinen | 435/29 |
| 4,946,777 | 8/1990 | Lameris et al. | 435/29 |
| 5,196,313 | 3/1993 | Culbreth | 435/32 |
| 5,206,151 | 4/1993 | Robertson | 435/32 |

OTHER PUBLICATIONS

Bitton, G., et al., "Tetrazolium Reduction–Malachite Green Method for Assessing the Viability of Filamentous Bacteria in Activated Sludge," *Appl. and Envir. Microb.*, vol. 43, No. 4, pp. 964–966 (1982) Month Not Available.

Bitton, G., et al., "Toxicity Testing Using Microorganisms," CRC Press, Boca Raton FL, pp. 28–54 (1986) Month Not Available.

Bitton, G., et al., "Bakers' Yeast Assay Procedure for Testing Heavy Metal Toxicity," *Bull. Environ. Contam. Toxicol.*, vol. 32, pp. 80–84 (1984) Month Not Available.

Bochner, B.R., et al., "Generalized Indicator Plate for Genetic, Metabolic and Taxonomic Studies with Microorganisms," *Applied Envir. Microb.*, vol. 33, pp. 434–444 (1977) Month Not Available.

Botsford, J.L., "An Assay for Toxic Chemicals Using Microorganisms," *Divining Rod*, New Mexico Water Resources Research Institute, p. 3 (Summer 1995) Month Not Available.

Felton, J.S., et al., "The Mouse Oocyte Toxicity," *Environ. Sci. Res.*, vol. 27 pp. 245–255 (1983) Month Not Available.

Liu, D., "A Rapid Biochemical Test for Measuring Chemical Toxicity," *Bull. Environm. Contam. Toxicol.*, vol. 26, pp. 145–149 (1981) Month Not Available.

McFeters, G.A., et al., "A comparison of Mirobial Bioassays for the Detection of Aquatic Toxicants," *Water Res.*, vol. 17, No. 12, pp. 1757–1762 (1983) Month Not Available.

(List continued on next page.)

*Primary Examiner*—Louise N. Leary
*Attorney, Agent, or Firm*—Jeffrey D. Myers; Deborah A. Peacock; D. Goelet Kehl

[57] ABSTRACT

A microbiological assay for chemicals, which uses a cell and a reducing dye to quantitatively measure inhibition of electron transport in the cell membrane as a function of chemicals in the substance being tested, is disclosed. This assay and method is reliable, simple, fast, and inexpensive, requires a minimum amount of durable equipment, and avoids the need for the use of live animals as the indicator organisms. The assay is particularly useful for testing for toxicity in food products, environmental, medical and industrial processes, sewage treatment, effluent, agricultural wastes, and chemical dumps.

37 Claims, 6 Drawing Sheets

OTHER PUBLICATIONS

Mathews, C.K., et al., "Chap 15 Biological Oxidations, Electron Transport, and Oxidative Phosphorylation," *Biochemistry*, Benjamin/Cummins Publishing Co., Inc., pp. 523–525 (1990) Month Not Available.

Mueller, J.G., et al., "Biodegradation of Creosote and Pentachlorophenol in Contaminated Groundwater; Chemical and Biological Assessment," *Appl and Environ Michorb*, vol. 57 No. 5 pp. 1277–1285 (1991) Month Not Available.

Ribo, J.M., et al., "Effects of Selected Chemicals to Photoluminescent Bacteria and their Correlations with Acute and Sublethal Effects on Other Organisms," *Chemosphere*, vol. 12, No. 11/12 pp. 1421–1442 (1983) Month Not Available.

Smith, S.N., et al., "Evaluation of Dehydrogenase as a Suitable Indicator of Soil Microflora Activity," *Enzyme Microb. Technol.*, vol. 1, pp. 279–281 (1979) Month Not Available.

Tchan, Y.T., et al., "Bioassay of Herbicides by Bioluminescence," *Acta Phytopathologia Academiae Sci. Hung.* vol. 12, No. 1–2, pp. 3–11 (1977) Month Not Available.

Thomulka, K.W., et al., "Detection of Biohazardous Materials in Water by Measuring Biolouminescence Reduction with the Marine Organism," *J. Environ. Sci. Health*, vol. A28, No. 9, pp. 2153–2166 (1993) Month Not Available.

Van De Sandt, J.J.M., et al., Cutaneous Toxicity Testing in Organ Culture: Neutral Red Uptake and Reduction of Tetrazolium Salt (MTT), *Toxic. In Vitro*, vol. 7, No. 1, pp. 81–86 (1993) Month Not Available.

Advertisement: PerSeptive Biosystems, Biosearch Products (1994) Month Not Available.

Brierley, G.P., *Ann Arbor Science*, pp. 397–407 (1977) Month Not Available.

Casida, Jr., L. E., et al., *Soil Science*, vol. 98, pp. 371–377 (1964) Month Not Available.

Dutton, R.J., "Use of Tetrazolium Salt (INT) for Enumeration of Active Bacteria and Toxicity Testing in Aquatic Environments," M.S. Thesis *University of Florida*, Gainesville Fl (1984) Month Not Available.

Felton, J.S., et al., *Short–Term Bioassays in the Analysis of Complex Environmental Mixtures*, vol. III, pp. 245–260 (1983) Month Not Available.

Green, J.C., et al., "A Cmparison of 3 Microbial Assay Procedures for Measuring Toxicity of Chemical Residues," *Arch. Environ. Contam. and Toxicol.*, vol. 14, pp. 569–667 [YEAR?] Month Not Available.

Idos, L., *Canadian Journal of Microbiology*, vol. 5, pp. 245–250 (1959) Month Not Available.

Jones, P.H., et al., *Journal of Water Pollution Control Fed.*, vol. 41, pp. R441 (1969) Month Not Available.

Lehnard, G., *Water Resources*, vol. 2, pp. 161–165 (1968) Month Not Available.

Lehnard, G., *Hydrobiologia*, vol. 25, pp. 1–9 (1963) Month Not Available.

Merck Index, *Merck & Co., Inc.*, Rahway NJ (1968) passage 1.476 gm (1ml) is soluble in 200 ml water, equivalent to 7.38 mg/ml, Month Not Available, p. 243.

Otoguro, et al., *ATLA* vol. 19, pp. 352–360 (1991) Month Not Available.

Rhuling, A., et al. *Oikos*, vol. 24, pp. 402–406 (1973) Month Not Available.

Stevenson, I.L., *Canadian Journal of Microbiology*, vol. 8, pp. 371–375 (1959) Month Not Available.

Sun, B., "Comparison of Inter Species Toxicity of Organic Chemicals and Evaluation of QSAR Approaches in Toxicity Prediction," M.S. Thesis, Environmental Engineering, *New Mexico State University* (1993) Month Not Available.

Eidus, L., "Observations on the Use of Tetrazolium salts in the Vital Staining of Bacteria," *Canadian Journal of Microbiology*, vol. 5, No. 3, (Jun., 1959), pp. 245–250.

Stevenson, I. L., "Dehydrogenase Activity in Soils," *Canadian Journal of Microbiology*, vol. 5 (1959), pp. 229–236, Month Not Available.

ASSAY FOR CHEMICALS

BACKGROUND OF THE INVENTION

1. Field of the Invention

The present invention relates to a method for detecting the presence and concentration of toxic compounds, in water and solid materials. More particularly, the present invention relates to an assay that involves adding a microorganism and an indicator dye to the material being tested and measuring the inhibition of reduction of the indicator dye.

2. Background Art

Indicator organisms must be used to assay for toxic chemicals, because toxicity is defined by the damage done to living organisms by the toxin. Some assays for toxic chemicals involve use of live animals as the indicator organism. Acute toxicity is judged by the ability of the animal to survive exposure to a given concentration of the toxic chemical for a defined time. Chronic toxicity is judged by the ability of the animal to reproduce normal offspring. These tests require elaborate facilities to maintain the animals in a constant environment. The tests themselves are slow, expensive, and require highly skilled personnel to carry out. The use of animals to test for toxic chemicals has been criticized by animal rights advocates.

Alternatives to animal assays have been sought. There is an assay using mitochondria isolated from beef hearts at the slaughter house. This assay cannot be carried out in a modestly equipped laboratory by relatively unskilled personnel (G. P. Brierley, *Ann Arbor Science*, pp. 397–407 (1977)).

Recently a variety of assays using animal cells grown in vitro in the laboratory have been used to assay for toxic chemicals. Mouse oocytes have been used (J. S. Felton, R. L. Dobson, *Short-term Bioassays in the Analysis of Complex Environmental Mixtures*, Vol. III, pp. 245–260 1983)). A similar test using cutaneous cells in organ culture, has been reported (J. VanDersandt, A. Rutten, and H. Koeter, *Toxicology in Vitro* Vol. 7, pp. 81–86 (1993)). These tests are readily carried out in laboratories that culture animal cells in vitro. But this takes a great deal of equipment and expertise that is not available in a modestly equipped laboratory.

There is a report of using the reduction of a tetrazolium dye (as used in this patent) by rat hepatocytes (K. Otoguro, K. Komiyama, S. Omura, C. A. Tyscon, ATLA Vol 19, pp 352–360, 1991). This shows that tetrazolium can be reduced by all cells having electron transport. There is also an assay that relies of the ability of toxic chemicals to interfere with the ability of cells to adhere to a glass surface. This is marketed as "CytoFlourII™" by PerSeptive Biosystems, Biosearch Products, of Bedford, Mass. The literature for the assay describes an "enzyme-amplified" approach, in which a quantitative flourescence assay monitors changes in the residual flourescence signal emitted from labeled cells. A flourogenic substrate is used to improve the performance of the assay. Flourimeters used to measure florescence are complicated, expensive instruments. Again, it is doubtful that this assay can be carried out in a modestly equipped laboratory by ordinary personnel.

There is one test using ATPase, an enzyme complex that breaks down ATP. The enzyme is mixed with the toxic chemical and ATP, the substrate for the enzyme, is added. Many toxic chemicals inhibit the activity of this complex enzyme. The ATP left after the reaction is measured using a second enzyme, lucifrase. Lucifrase includes a pigment that fluoresces in response to ATP. The florescence can be measured with a luminometer (G. Bitton, B. J. Dutka, *Toxicity testing using microorganisms*, pp. 163 (1986)). Any test involving two enzyme reactions (the ATPase and the lucifrase reactions) is complex.

There are many tests using bacteria as the indicator organism. Toxic compounds inhibit the growth of bacteria. Toxic compounds inhibit various metabolic activities in the bacteria. Bacteria are easily grown. This approach can be inexpensive.

The Microtox™ test is marketed by the Microbics Corporation of Carlsbad, Calif. This assay uses the bioluminescent marine bacterium *Photobacterium harveyi* as the indictor organism. This bacterium glows in the dark using a florescent pigment as a terminal electron acceptor. In bacteria, the mechanism for electron transport is associated with the cytoplasmic membrane. There are many enzymes, cofactors, and electron carriers that are juxtaposed on the membrane. Any alteration of the membrane will alter this arrangement of the components of the electron transport system and will inhibit electron transport. This inhibition will result in less light produced by the bioluminescent pigment. The assay requires special equipment, a refrigerated incubator and a luminometer.

There is a variation of this assay. The bioluminescent bacterium and a cyanobacterium are mixed. The toxic chemical is added. The toxic chemical inhibits growth of cyanobacterium. This inhibits production of oxygen. The lower oxygen inhibits growth and luminescence of the bioluminescent bacterium (Y. T. Tchan, C. M. Chiou ACTA Phytopath, *Acad. Sci.* Vol. 12, pp. 3–1, 1977). K. W. Thomulka and D. J. McGee have proposed a similar assay using another bioluminescent bacterium *Vibrio harveyii* (*Jour. Environ. Sci. Health.* A28(9) 2153–2166, 1993).

There are many other tests using bacteria to measure toxic chemicals (G. Bitton, B. J. Dutka, *Toxicity testing using microorganisms*, pp. 163 (1986)). Most are based on inhibition of growth by the toxic compound. Growth is usually estimated by following consumption of oxygen with an oxygen electrode. Some follow growth spectophotometrically.

Polytox™, marketed by the Polybac Corporation of Bethlehem, Pa., uses an artificial consortium of 12 bacteria added to sample flasks. The bacteria degrade the toxic chemical, using it as a source of energy. The oxygen consumed by the bacteria is measured with an oxygen electrode. Alternatively, the ammonium released by degradation can be measured with the ammonium electrode. The samples are large and can require several days incubation. Both the oxygen and ammonium electrodes are expensive and difficult to work with. This test has been used primarily to design bioremediation programs using this consortium of bacteria to degrade toxic chemicals.

There are several microbial assays using chemical indicators. A chemical, a pH indicator or an oxidation-reduction indicator, is combined with the bacterial cells and the toxic chemical. The indicator changes color in response to metabolic activity in the bacteria. If the toxic chemical inhibits the metabolic activity, the change in color is inhibited. U.S. Pat. No. 4,929,546 to Mayra-Makinen discloses a method for determining the presence of an antibiotic in milk, using an indicator microorganism and a pH (acid-base) indicator.

There is one test in which the reduction of the dye resazurin (oxidation-reduction) is measured using *Escherichia coli* or the bacteria in activated sewage sludge as the test organism (O. Liu, *Bulletin of Environmental Contamination Toxicology*, Vol.26, pp. 145–149 (1981)). This dye works very slowly.

There are several assays using tetrazolium dyes. U.S. Pat. Nos. 3,043,751 and 3,197,384 to Goldman disclose use of a tetrazolium dye tetrazolium to measure the growth of microorganisms and to determine the effectiveness of antibiotics capable of killing the microorganisms. Tetrazolium dyes can be reduced by bacteria resulting in a dynamic color change and precipitation of the dye. U.S. Pat. No. 3,107,204 to Brown describes a method for determining microbiological susceptibility to antibiotics which involves incubation of the microorganisms in the presence of a tetrazolium dye and the antibiotic. U.S. Pat. No. 3,126,325 to Poole discloses a similar test. U.S. Pat. Nos. 3,941,658 and 4,946,777 to Llameris disclose methods for detecting the presence of an antibiotic material in food material, using an antibiotic-sensitive microorganism and a tetrazolium dye. U.S. Pat. No. 5,206,151 to Robertson discloses the use of a redox dye, like tetrazolium, that is reduced to determine the minimum amount of biocide required to treat microbiologically contaminated systems.

Tetrazolium dyes have been used to determine the viability of bacteria in activated sewage sludge. L. Idos, B. Biena, and L. Greenberg, *Canadian Journal of Microbiology*, Vol. 5, pp. 245–250 (1959); G. Bitton and B. Koopman, *Applied and Environmental Microbiology*, Vol. 43, pp. 964–966 (1982). The bacteria suspended in dilute solution of the dye and are observed under the microscope. Viable bacteria reduce the dye causing it to precipitate. The precipitate around the cell is visible microscopically. Tetrazolium dyes have been used to estimate reducing potential in the soil. The dye is added to a soil suspension. If the soil includes many viable bacteria, the dye is reduced, changes color dramatically. This color change can be measured readily with a simple spectrophotometer. L. E. Casida Jr., D. A. Klein, and T. Stantoro, *Soil Science*, Vol. 98, pp. 371–377 (1964). P. H. Jones and O. Prasad, *Journal of Water Pollution Control Fed.*, Vol. 41, pp. R441 (1969). S. N. Smith and G. J. F. Pugh, *Enz Microb Tech*, Vol. 1, pp. 279 (1979), and I. L. Stevenson, *Canadian Journal of Microbiology*, Vol. 8, pp. 371–375 (1959). The dehydrogenase activity (a reflection of the activity of the bacteria present) in sewage has been estimated using tetrazolium dyes (G. Lehnard, *Water Resources*, Vol. 2, pp. 161–165 (1968); G. Lehnard, *Hydrobiologia*, Vol. 25, pp. 1–9 (1963)).

Triphenyl tetrazolium (TTC) has been used to measure the dehydrogenase activity of bacteria in sludge to estimate the toxicity of additions to soil or activated sludge (G. Bitton and B. J. Dutka, *Toxicity testing using microorganisms*, pp. 163 (1986)). There is a report of estimating the toxicity of heavy metals in sludge using reduction of TTC (A. Rhuling and G. Tyler, *Oikos* Vol. 24, pp. 402–406 (1973)). TTC reduction is oxygen sensitive, so the experiments must be run under anaerobic conditions. TTC reduction could not be used in a modestly equipped laboratory.

There is a report of the reduction of a tetrazolium dye using Baker's yeast (G. Bitton, B. Koopman, and H. O. Wang, *Bulletin of Environmental Contamination Toxicology*, Vol. 32, pp. 80–90 (1984)). This test was used to measure the toxicity of heavy metals. This approach has been used with the bacterium *Pseudomonas fluorescens* to estimate viable bacteria and to estimate the toxicity of heavy metals in an offshore marine site (R. J. Dutton, *Use of tetrazolium salt (INT) for enumeration of active bacteria and toxicity testing in aquatic environments*, M. S. Thesis, University of Florida, Gainesville, Fla., (1983)).

None of these test using tetrazolium included studies of a variety of toxic compounds. None of them are cited in the toxicology literature. The only test using microorganisms that is cited in the literature is the Microtox test using the bioluminescent marine bacteria. These other methods are not used.

There is a need for a fast, simple, inexpensive test for toxic chemicals, which can be carried out in a modestly equipped laboratory by personnel without special training. Conventional testing for toxicity is very expensive, thousands of dollars per test, and is only performed where there is a good reason to suspect toxicity. There is mounting evidence in studies of bioremediation that the chemical of interest can be broken down and can no longer be detected using sophisticated chemical tests yet the degradation products are toxic. (J. G. Mueller, D. P. Miaddaugh, S. E. Santz, P. J. Chapman, "Biodegradation of Creotsote and Pentacholorphenol in Contaminated Ground Water: Chemical and Biological Assessment," *Applied and Environ. Microbial.* 57: 1272–1285 (1991). Soils need to be routinely tested to monitor degradation of agricultural chemicals. Water quality should be monitored routinely. There is recent interest in detecting toxic algal blooms in reservoirs. Mine wastes, industrial wastes, and oil drilling waste pools all need to be monitored.

Since the available tests for toxic chemicals are expensive or require elaborate facilities and highly trained personnel, toxicity testing is not usually performed unless required legally. If there are unsuspected toxic chemicals present, there will be no legal pressure to assay for toxic chemicals. For example, determining the half life of the coxicity of agricultural chemicals would be valuable. There is no simple, inexpensive, rapid way to carry these sorts of tests out. A good "first case" assay, to simply be able to determine if a chemical could be toxic and should be examined further would be useful.

There is no one test for toxic chemicals that detects all toxic chemicals. Several tests must be available. There is a report of the toxicity of 2-chlorophenol using 8 different assays. The toxicity varied by three orders of magnitude (J. M. Ribo, K. L. E. Kaiser, "Effects of isolated chemicals to photoluminescent bacteria and their correlations with acute and sublethal effects on other organisms", *Chemosphere* 12: 1421–1442, 1983). At the very least, the test described in this patent application offers a simple, inexpensive test that can be run with other tests.

SUMMARY OF THE INVENTION

The present invention is of a method of testing for toxicants in a substance comprising: adding a cell to the substance to form a mixture; adding to the mixture a dye which undergoes chemical reduction in the presence of the cell; and quantitatively measuring inhibition of electron transport in the cell as a function of toxicants in the mixture. In the preferred embodiment, the toxicants are chemicals, compounds, toxic substances, minerals, or mixtures thereof, including hydrocarbons, solvents, metals, and salts. Where the dye changes color during reduction, measuring comprises monitoring the color change produced by reduction. Measuring may include measuring absorbance of the dye (at a wavelength chosen based on the dye being used, such as 550 nm or 590 nm, preferably by spectrophotometer) into the cell during chemical reduction and calculating the concentration of toxicants in the mixture from absorbance data obtained. The cell is preferably a bacterial cell, such as *Bradyrhyzobium japonicum*, *Pseudonomonas fluorescens*, *A. Arthrobacter crystallopoites*, *Salmonella typhimurium*, *Bacillus megaterium*, *Rhizobium meliloti*, *Rhizobium leguminosarum*, *Escherichia coli*, *Streptococcus lactis*, or Rhodopseudonomas sphaeroides. However, the cell may be a plant, fungus, yeast, or animal. The dye preferably comprises TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxyl(1, 1'-biphenyl)-4,4'-diyl]-bis(2,5-diphenyl-2H-tetrazolium) dichloride); MTT (3-[4,5-dimethylthiazol-2-yl]-2,5-diphenyl tetrazolium bromide); or NBT, Nitro blue tetrazolium (2,2'-di-nitrophenyl-5,5'-3,3'-(3,3'-dimethoxy-4, 4'-diphenylene)ditetrazolium chloride), most preferably MTT. Adding a cell to the substance being tested may include growing the cell by inoculating a culture with an inoculum of cells (preferably not more than 36 hours old and preferably in a medium supplemented with an amino acid) and harvesting the cell. The cell may be washed or unwashed. The method may be conducted in a solution comprising water and/or a buffer, and may be conducted in an aerobic or an anaerobic environment. The mixture is preferably incubated for a sufficient time to substantially complete reduction.

The present invention is also of a method of testing for toxicants in a substance comprising: adding a cell to the substance to form a mixture; adding to the mixture a dye which undergoes chemical reduction in the presence of the cell and changes color; incubating the mixture during reduction of the dye; quantitatively measuring a change in color intensity of the dye during incubation, the change being indicative of the inhibition of electron transport and the decrease in reduction of the dye over time; and calculating the concentration of toxicants in the mixture from data obtained. The cell is preferably a bacterial cell such as Bradyrhyzobium japonicum, Pseudonomonas fluorescens, A. Arthrobacter crystallopoites, salmonella typhimurium, Bacillus megaterium, Rhizobium meliloti, Rhozobium leguminosarum, Escherichia coli, Streptococcus lactis, or Rhodopseudonomas sphaeroides. However, the cell may be a plant, fungus, yeast, or animal. The dye preferably comprises TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxy(1, 1'-biphenyl)-4,4'-diyl]-bis(2,5-diphenyl-2H-tetrazolium) dichloride); MTT (3-[4,5-dimethylthiazol-2-yl]-2,5-diphenyltetrazolium bromide); or NBT, Nitro blue tetrazolium (2,2'-di-nitrophenyl -5,5'-diphenyl-3,3'- (3,3'-dimethoxy-4,4'-diphenylene)ditetrazolium chloride). Adding a cell to the substance preferably includes suspending the mixture in buffer, and the incubation preferably is performed in minutes with the mixture at 30° C. Measuring preferably comprises measuring a first absorbance of the dye into the cell at time=0; sequentially measuring absorbance of the dye during the incubation; subtracting the first absorbance from a final absorbance determined by an end point of absorbance established from the sequential measuring; obtaining from the subtracting an absorbance difference to be used in the calculating; and plotting the absorbance difference on a Y axis against the toxicants in the substance being tested on an X axis. The plotting preferably comprises plotting the absorbance difference against a concentration of the toxicants in the substance being tested and/or plotting the absorbance difference against a volume of the toxicants in the substance being tested. Calculating preferably comprises: plotting the data against the toxicants in the substance being tested; calculating and fitting a regression line to the data; determining a slope, a Y-intercept, and a regression coefficient from the regression line; establishing the toxicity of the toxicants by calculating a concentration of toxicants resulting in a percentage decrease in reduction of the dye, from the slope and the Y-intercept of the regression line, using an equation, Y/2=mX+B, where Y equals the absorbance of a control sample without a toxicant, m is the slope of the regression line, B equals the Y-intercept, and X equals the concentration of toxicants; and expressing the concentration to quantitate the toxicity of the toxicants. Plotting preferably comprises plotting the data against a concentration of toxicants in the substance being tested, and comprises solving the equation for $$X = \frac{Y/2 - B}{m}, \text{ or}$$

plotting the data against a volume of toxicants in the substance being tested, and calculating comprises solving the equation for $$\log X = \frac{Y/2 - B}{m}$$

and calculating the antilog of log X to determine the concentration of toxicant.

The present invention is further of a method of testing for the presence of toxicants in a substance comprising: adding a cell to the substance being tested to form a mixture; suspending the mixture; measuring absorbance in the mixture at an appropriate wavelength at time=0; adding to the mixture a dye capable of chemically reducing and changing color in the presence of the cell; incubating the mixture, thereby causing reduction of, and a resulting color change in, the dye; measuring absorbance of the dye in the cell membrane during the incubation, the absorbance decreasing over time from the time=0 absorbance to an endpoint absorbance equivalent to an endpoint of substantial reduction of the dye, as demonstrated by a change in color intensity of the dye over time; subtracting the time=0 absorbance from the endpoint absorbance to arrive at an absorbance difference; plotting the total absorbance on a Y axis versus the toxicants on an X axis; calculating a regression line, and thereby determining a slope of the line, a Y intercept, and a regression coefficient; solving an equation Y/2=mX+B for an X value, where Y is the absorbance of a control sample without a toxic chemical, m is the slope, B is the Y intercept, and X is a concentration of toxicant causing a percentage decrease in reduction of the dye; and calculating the X value to quantify the toxicity of the toxicants in the substance being tested. In the preferred embodiment, the cell is a bacterial cell such as Bradyrhyzobium japonicum, Pseudonomonas fluorescens, Arthrobacter crystallopoites, Salmonella typhimurium, Bacillus megaterium, Rhizobium meliloti, Rhizobium leguminosarum, Escherichia coli, Streptococcus lactis, or Rhodopseudonomas sphaeroides. However, the cell may be a plant, fungus, yeast, or animal. The dye preferably comprises TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxy (1,1'-biphenyl)-4,4'-diyl]-bis(2,5-diphenyl-2H-tetrazolium) dichloride); MTT (3-[4,5-dimethylthiazol-2-yl]-2,5-diphenyltetrazolium bromide); or NBT, Nitro blue tetrazolium (2,2'-di-nitrophenyl -5,5'-diphenyl-3,3'-(3,3'-dimethoxy-4,4'-diphenylene)ditetrazolium chloride).

The present invention is further of an assay for detecting toxicants in a substance comprising: a cell provided from the substance; a dye capable of chemically reducing in the presence of the cell when mixed with the cell; and means for quantitatively measuring inhibition of electron transport in the cell as a function of toxicants in the mixture. The cell is preferably a bacterial cell such as *Bradyrhyzobium japonicum, Pseudonomonas fluorescens, Arthrobacter crystallopoites, Salmonella typhimurium, Bacillus megaterium, Rhizobium meliloti, Rhizobium leguminosarum, Escherichia coli, Streptococcus lactis,* or *Rhodopseudonomas sphaeroides.* However, the cell may be a plant, fungus, yeast, or animal. The dye preferably comprises TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-|3,3'-dimethoxy (1,1'-biphenyl)-4,4'-diyl|-bis(2,5-diphenyl-2H-tetrazolium) dichloride); MTT (3-|4,5-dimethylthiazol-2-yl|-2,5-diphenyltetrazolium bromide); or NBT, Nitro blue tetrazolium (2,2'-di-nitrophenyl-5, 5'-diphenyl-3,3'-(3,3'-dimethoxy-4,4'-diphenylene)ditetrazolium chloride).

The present invention is also of an assay for detecting a chemical in a substance comprising: a viable microorganism; an indicator dye which reduces and changes color in the presence of the microorganism; means for obtaining absorbance measurements indicative of the amount of reduced dye in the substance being tested as a function of the color produced in the dye; and means for quantitating the concentration of chemical in the substance being tested using the absorbance measurements. The cell is preferably a bacterial cell such as *Bradyrhyzobium japonicum, Pseudonomonas fluorescens, Arthrobacter crystallopoites, Salmonella typhimurium, Bacillus megaterium, Rhizobium meliloti, Rhizobium leguminosarum, Escherichia coli, Streptococcus lactis,* or *Rhodopseudonomas sphaeroides.* However, the cell may be a plant, fungus, yeast, or animal. The dye preferably comprises TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-|3,3'-dimethoxy(1,1'-biphenyl)-4,4'-diyl|-bis(2,5-diphenyl-2H-tetrazolium)dichloride); MTT (3-|4,5-dimethylthiazol-2-yl|-2,5-diphenyltetrazolium bromide); or NBT, Nitro blue tetrazolium (2,2'-di-nitrophenyl-5,5'-diphenyl-3,3'-(3,3'-dimethoxy-4,4'-diphenylene) ditetrazolium chloride).

It is the primary object of this invention to provide a simple, inexpensive, rapid test for toxic chemicals using bacteria as the indicator organism. The effect of the toxic chemical on the metabolic activity of the bacteria will be followed using dyes that are reduced by the bacterium. This invention overcomes the above-noted disadvantages of other known assays.

Another object of the present invention is to provide a method of testing for chemicals that is reliable, simple, fast, and inexpensive, that requires a minimum amount of durable equipment, and that avoids the need for the use of live animals as the indicator organism. A useful assay should further be able to be performed by laboratory personnel without special training.

A further object of the present invention is to provide a versatile and effective method of testing for toxicity in food products, environmental samples, medical and industrial processes, sewage treatment, effluent from industrial plants, agricultural wastes, chemical dumps and in other applications.

The limitations associated with existing microbiological assays are overcome by the present invention which provides a microbiological test for chemicals. Cells mixed with the material being tested, a dye, which is reduced, is added. Inhibition of this reduction is proportional to the concentration of the toxic chemical. This reduction of the dye can be measured using a simple spectrophotometer at the wave length appropriate to the dye (450 to 650 nm).

The subject invention is simple enough and rapid enough to permit tests to be run frequently and routinely. The assay of the invention can be performed in a modestly equipped laboratory, such as an "in-house" laboratory, by typical laboratory technicians with no specialized training. The speed of the test has allowed as many as 200 assays to be run in one day.

This test is also inexpensive. The dyes are available commercially. Reactions are run in disposable test tubes. The cells can be grown readily in an inexpensive defined medium with the addition of small amounts of casamino cells. Cells can be washed in a refrigerated preparative centrifuge or at room temperature in a simple clinical centrifuge, and the results are not dramatically affected. The test can be run using unwashed cells. The data can be analyzed using a simple pocket calculator. A computer program may be readily designed to analyze the data.

The assay is effective and reliable. The assay compares well to the performance of other assays for toxic chemicals. Because it is simple and inexpensive, it provides a "first look" at potentially toxic chemicals.

The dyes are not toxic. Non-pathogenic bacteria can be used.

Additional objects, advantages and novel features, and further scope of applicability of the present invention will be set forth in part in the detailed description to follow, taken in conjunction with the accompanying figures, and in part will become apparent to those skilled in the art upon examination of the following detailed description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying figures, which are incorporated into and form a part of the specification, illustrate several embodiments of the present invention and, together with the description, serve to explain the principles of the invention. However, these figures, as well as the following detailed description and the examples, are only for the purpose of illustrating a preferred embodiment of the invention and are not to be construed as limiting the invention. In the drawings:

FIGS. 3, 4, and 5 show curves representative of experiments with organic compounds; FIGS. 6, 7, and 8 show curves representative of experiments with pollutants connected with petroleum; FIG. 9 shows a curve representative of experiments with solvents; and FIGS. 10, 11, and 12 show curves representative of experiments with toxic minerals. The regression lines for these data are included. The data shown in these figures illustrate that no two chemicals provide the same curve;

Figure 3:
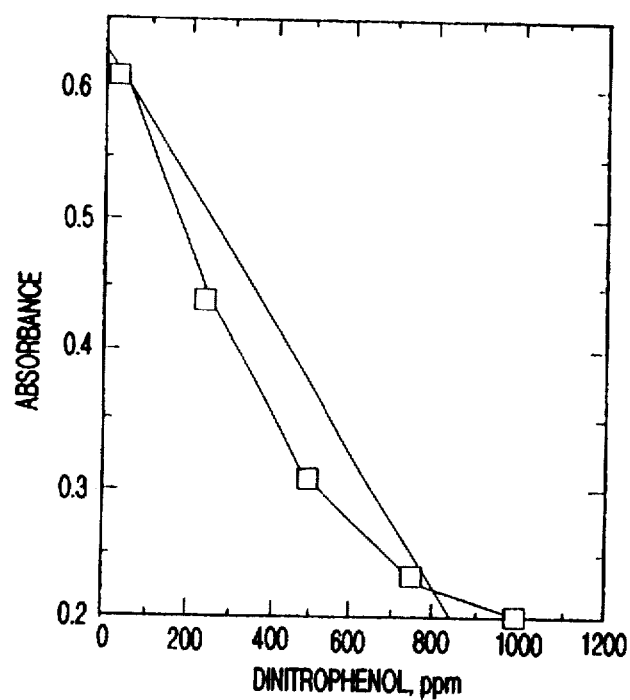
FIGS. 3 through 12 provide representative plots of curves from data obtained in experiments performed with the assay of the invention.
Figure 4:
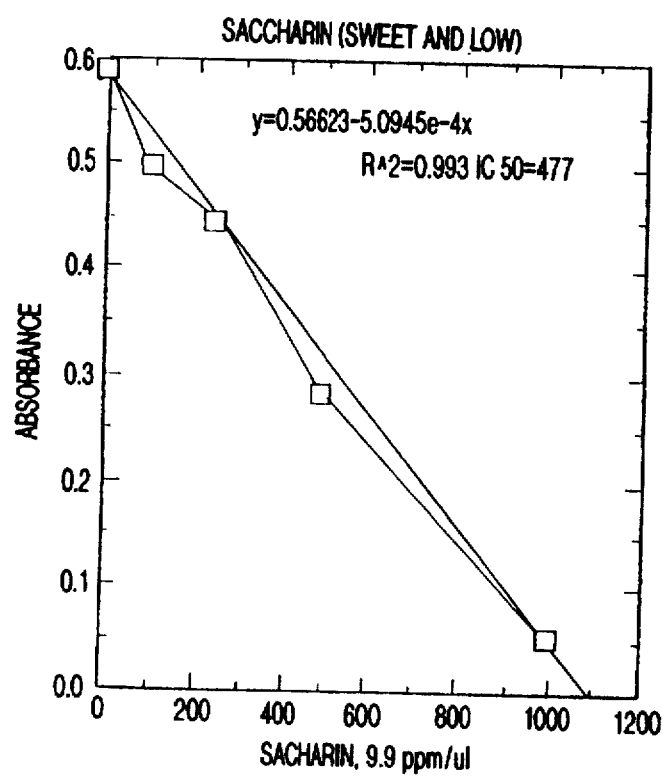
Figure 5:
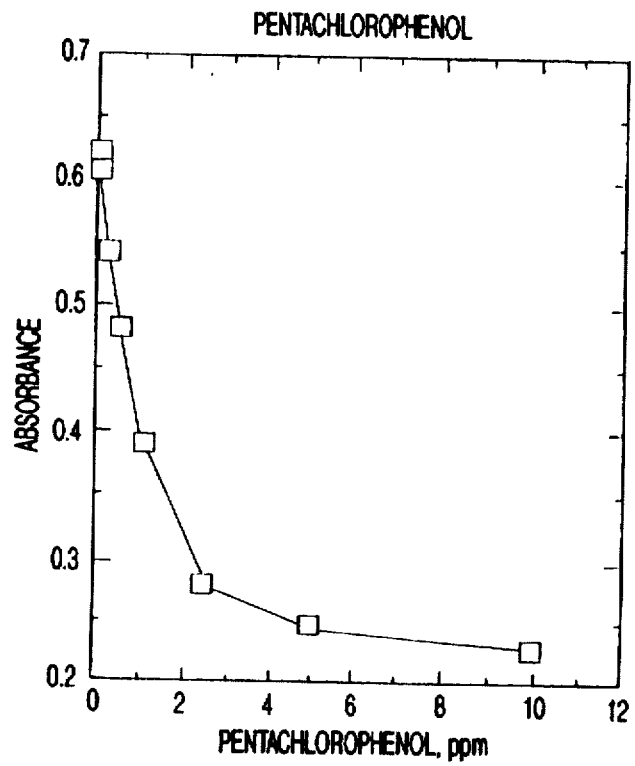
Figure 6:
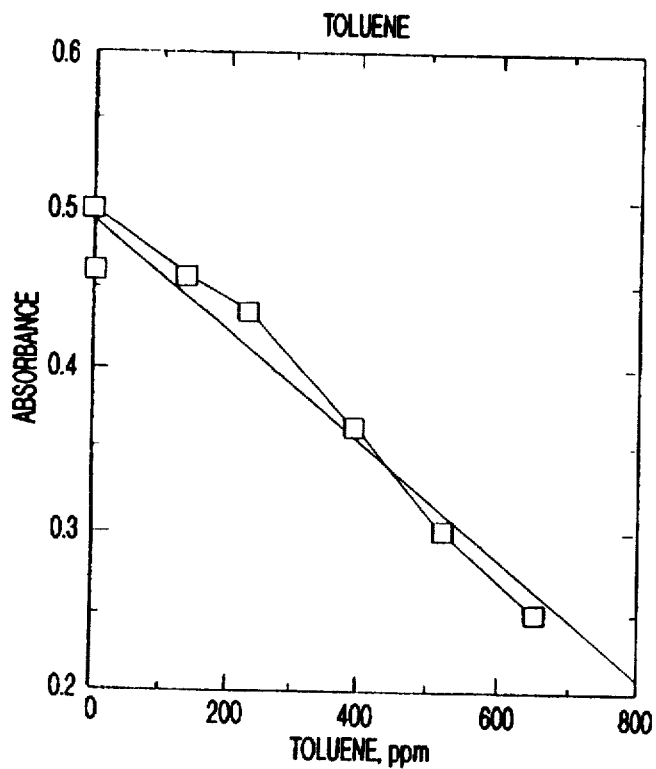
Figure 7:
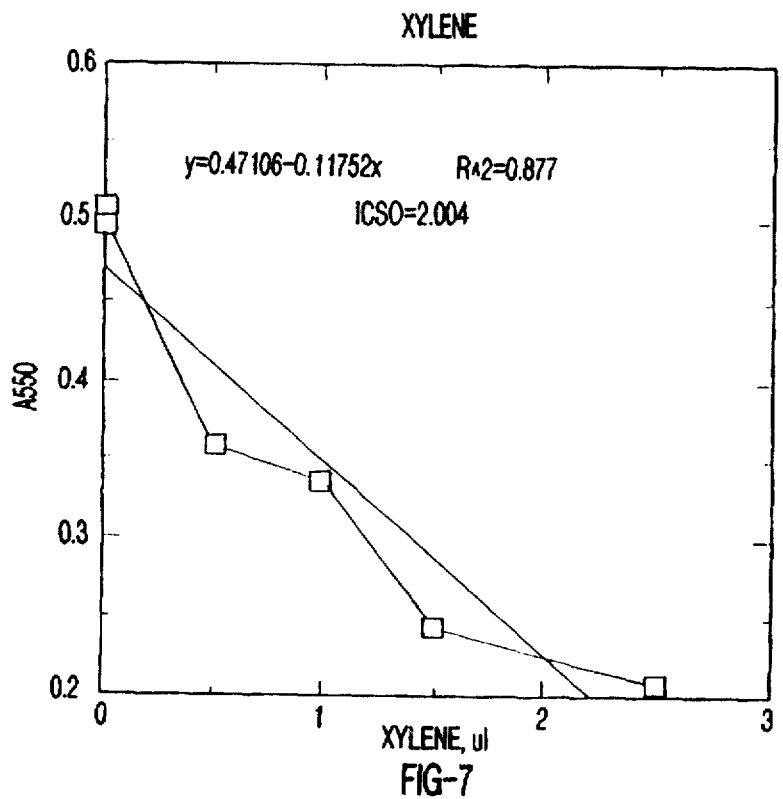
Figure 8:
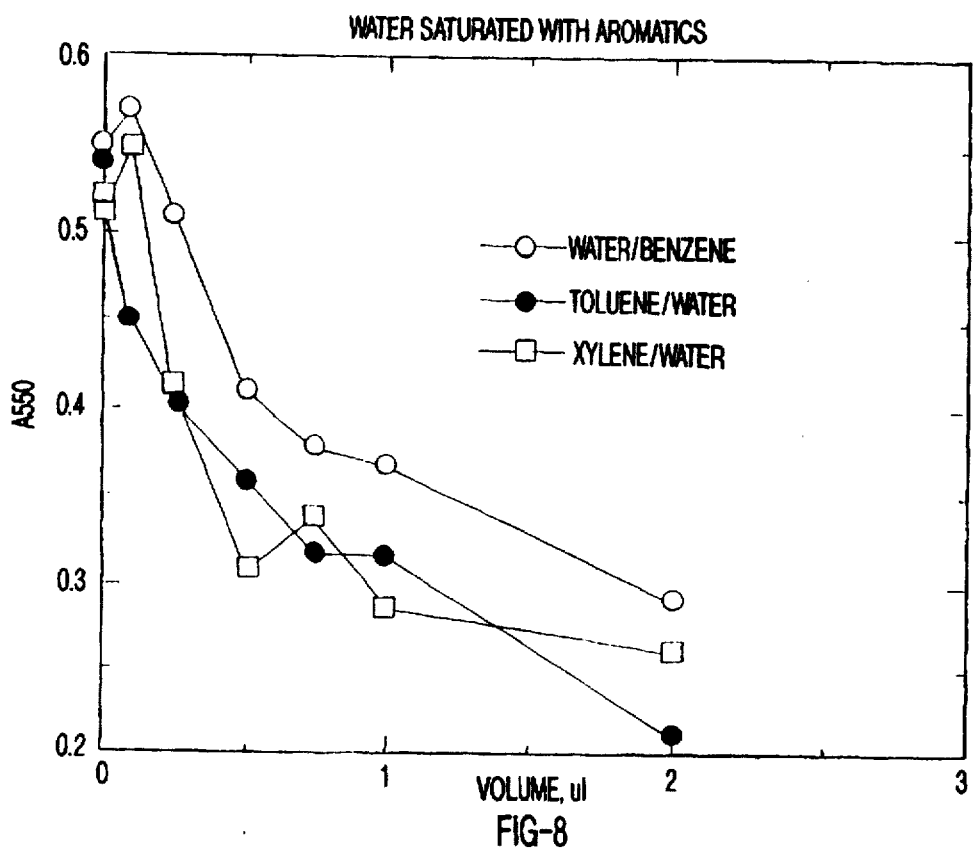
Figure 9:
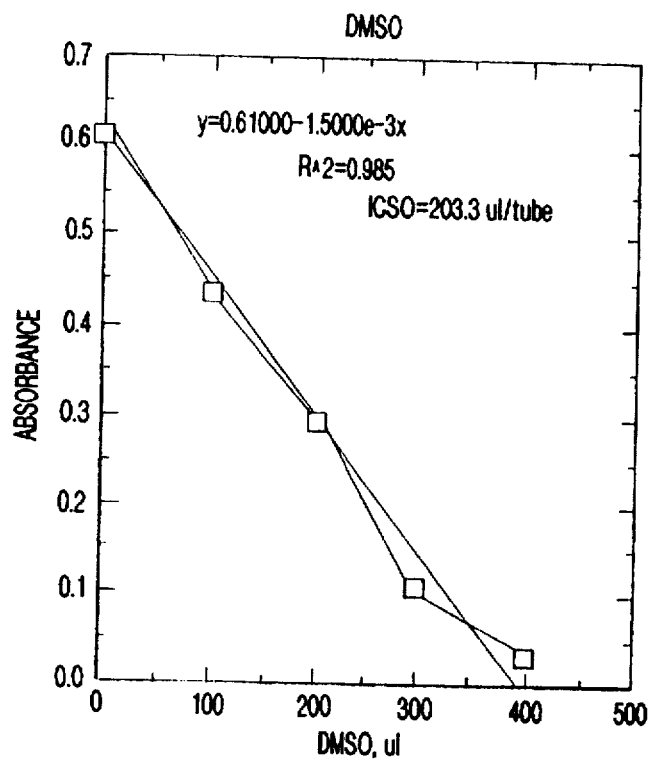
Figure 10:
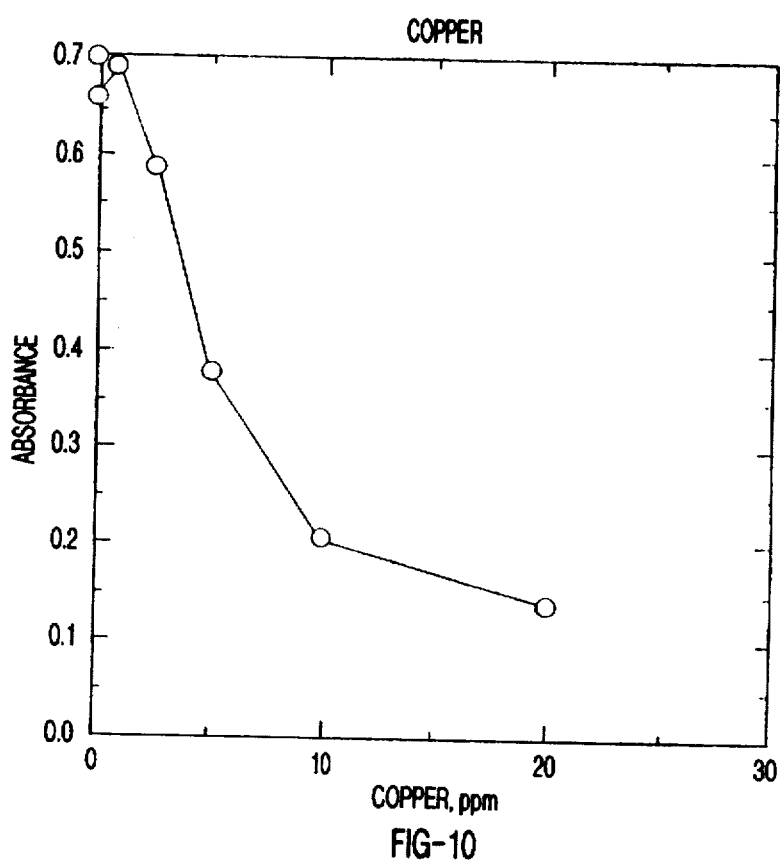
Figure 11:
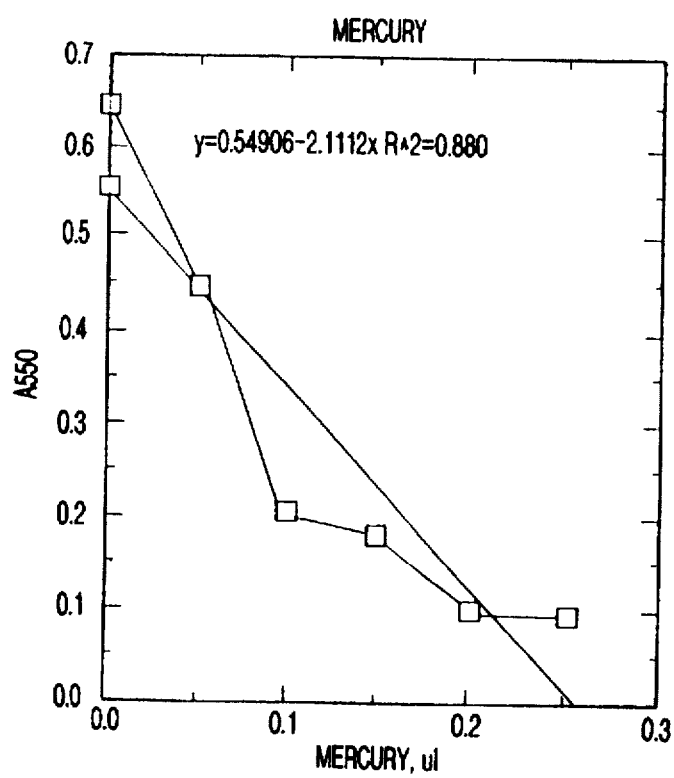

In particular, FIG. 3 demonstrates an assay of dinitrophenol;

FIG. 4 demonstrates an assay of saccharin;

FIG. 5 demonstrates an assay of pentachlorophenol;

FIG. 6 demonstrates an assay of toluene;

FIG. 7 demonstrates an assay of xylene;

FIG. 8 demonstrates an assay of benzene, toluene and xylene;

FIG. 9 demonstrates an assay of DMSO;

FIG. 10 demonstrates an assay of copper;

FIG. 11 demonstrates an assay of mercury; and

Figure 12:
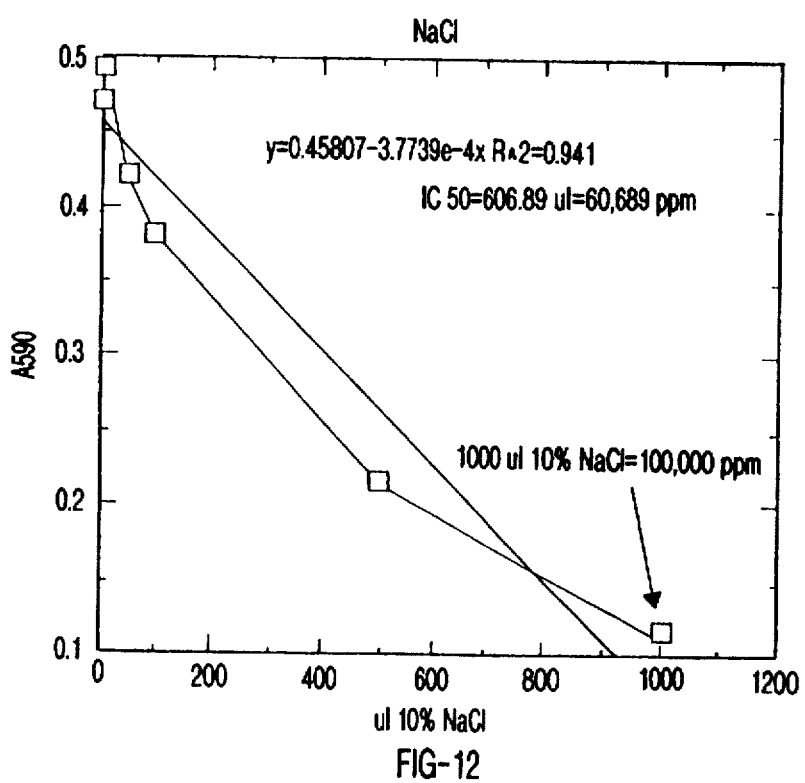

FIG. 12 demonstrates an assay of NaCl.

DETAILED DESCRIPTION OF THE INVENTION

The microbiological assay of the invention involves using a cell, more particularly a bacterium, such as $R.$ $meliloti$ or $E.$ $coli$, as the test or indicator organism to determine the presence, and concentration, of chemicals or elements in a substance. The term "chemicals" as used throughout the specification and claims is intended to include chemicals and their compounds, including toxic compounds, minerals, and elements. The term "toxicants" as used throughout the claims is intended to include all such chemicals.

The metabolic activity of the bacterium is estimated by following the reduction of a dye which reduces in the presence of the cell, more preferably a tetrazolium dye. The bacterium is mixed with the chemical and suspended in water or buffer in e.g., a test tube. The absorbance is measured at an appropriate wavelength for the dye being used at time=0, using e.g., a spectrophotometer. A tetrazolium dye, such as MTT (3-[4,5-Dimethylthiazol-2-yl]2,5-diphenyl-tetrazolium bromide) is added, and the tube is incubated, typically for about 20 minutes, at 30° C. The dye precipitates in the presence of the bacteria due to reduction, which causes the dye to become darkly colored. As the toxic chemical damages the cytoplasmic membrane of the cell, inhibiting electron transport, the intensity of the color of the dye is diminished. This reduction in color intensity, due to the inhibition of electron transport, can be measured using the spectrophotometer.

The absorbance of the dye is read sequentially (or continuously) for any changes (increase) until the absorbance stops increasing; the time period during which sequential absorbance readings are taken depends on the dye used. The time=0 absorbance is subtracted from the final absorbance, and this difference in absorbance between time=0 and the final absorbance is considered to be the "absorbance" used in calculations.

The results, in terms of change in absorbance, are plotted against the concentration of toxic chemical. A regression line is calculated and fitted to the data, and the concentration of toxic chemical reducing the absorbance by 50%, i.e., the concentration resulting in 50% inhibition of the reduction of the dye, is calculated from the slope and the Y-intercept of the regression line. The value calculated, called the IC50, is used to establish the toxicity of the chemical, and, expressed in parts per million (ppm), is used to quantitate the toxicity of the chemical. More specifically, reduction of the dye can be quantitated by the absorbance, for example for various dyes, at 590 nm.

The basic working principle of this invention is that bacteria reduce dye by electron transport. The electron transport system in bacteria is associated with the cytoplasmic membrane. Chemicals, particularly toxic chemicals, damage the cytoplasmic membrane of the cell; this also damages the membrane-associated mechanism affording electron transport, which in turn inhibits, or prevents, reduction of the tetrazolium dye. The damage is proportional to the concentration of the toxic chemical. For the assay, the concentration of toxic chemical is varied by using different volumes of the chemical or, alternatively, keeping the volume constant and using dilutions.

The assay of the invention can be carried out in a minimally equipped laboratory. The cells must be grown, harvested and washed requiring an incubator and centrifuge. The cells may be washed in a refrigerated preparative centrifuge or at room temperature in a clinical centrifuge with little effect on the results. Alternatively, the test may be performed with unwashed cells, and the results are very nearly the same as with washed cells. After washing, cells are routinely resuspended in a buffer (e.g., 0.01M phosphate buffer) but can be resuspended in water.

The test can be run in conventional test tubes (e.g., 13×110 mm disposable test tubes), using conventional pipettes. The reactions are carried out in a water bath (e.g., at 30° C.). The absorbance of the cells and the toxic chemical are measured at time=0 to correct for precipitates, for opaque samples, e.g., the aqueous extracts of motor oil are opaque, and for differences in the test tubes used. This test has the advantage that the absorbance at time=0 is easily taken.

The method of the invention is not limited to a particular type of dye. Tetrazolium dyes, resazurin, and DCIP (2,6-dichlorophenol-indophenol), are particularly useful, but any dye that will react with the chosen cell according to the protocol of the invention may be used with this assay. The absorbance of the dye can be read with a very simple spectrophotometer or any other means useful for absorbance measurements. The sample size is large enough to permit use of a "sipper" type spectrophotometer.

Typically, the reaction is essentially finished after a 20-minute incubation time. The absorbance tends to increase very slowly after this point. Incubation of samples for longer periods generally does not change results appreciably. The inhibition of reduction by chemicals appears to be irreversible.

After the incubation, the data are plotted, with the concentration or the volume of the chemical on the X-axis and the absorbance on the Y-axis. The data can be plotted versus the concentration of chemical, or it can be plotted versus the volume (in microliters) of the chemical used. Given the volume, and knowing the concentration of chemical in the stock, the concentration of the chemical in that volume can be computed.

Regression lines are calculated, and the slope of the line, the Y intercept, and the regression coefficient are determined using the equation, $Y/2=mX+B$, where Y is the absorbance of the control, i.e., the sample without a chemical, m is the slope of the regression line, B is the Y intercept (the value for Y when X=0) calculated from the regression line, and X is that concentration of chemical resulting in 50% inhibition of electron transport, or reduction of the dye, as estimated from the absorbance of the culture, also referred to as the IC50 (inhibitory concentration, 50%). This equation is solved:

$$X = \frac{Y/2 - B}{m}$$

Also, the log of the concentration of the chemical may be plotted versus the absorbance, using the following solution of the equation:

$$\log X = \frac{Y/2 - B}{m}$$

The antilog of log X is the concentration of chemical resulting in a 50% decrease in the absorbance. The data can be analyzed using either a pocket calculator or a computer system.

A preferred use for the assay of the invention is to determine the toxicity of organic compounds, solvents, and minerals. Another preferred use is to monitor toxic compounds of petroleum found in water extracts of used motor oil.

The present invention having been generally described, the following preferred specific embodiments are provided to illustrate some of the properties and demonstrate the practical advantages thereof, and to allow one skilled in the art to utilize the present invention to its fullest extent. These examples included are to be construed as merely illustrative, and not limitative of the remainder of the disclosure or the claims in any way whatsoever.

DESCRIPTION OF THE PREFERRED EMBODIMENT

The assay of the present invention was performed using ten species of bacterial cells: Rhizobium meliloti, Bacillus megaterium, Salmonella typhimurium, Streptococcus lactis, Bradyrhizobium japonicum, Rhizobium leguminosarum, Arthrobacter crystallopoites, Escherichia coli, Pseudonomonas fluorescens, and Rhodopseudomonas sphaeroides. These bacteria are readily available in the commercial market. R. meliloti, B. japonicum, and R. leguminosarum were grown in CDM medium supplemented with 0.1 casamino acids. A. crystallopoites was grown in $R_2A$ medium (Difco). E. coli was grown in LB medium (Difco) or in M63 medium with glucose or succinate as the carbon source. S. typhimurium and B. megaterium were grown in LB medium. S. lactis was grown in LB supplemented with 1% glucose.

Using R. meliloti as the representative example, it was found that cells could be harvested when the final absorbance was 0.6 to 2.2 with very little difference in the results. Cells were collected by centrifugation in a refrigerated preparative centrifuge and were washed once with 0.01M potassium phosphate buffer, pH 7.5. After washing, cells were resuspended in the phosphate buffer to an absorbance at 550 nm=0.3 (other absorbances, such as at 650 nm, may be used).

In a few experiments, cells were resuspended to a final absorbance of 3.0 in the Tris buffer; MOPS (pH 7.5, 0.1M) and 0.1 ml was used. With these 10× concentrated cells, 0.1 ml cells were used in the assay. This enabled a larger sample of the toxic chemical to be used. Cells were also resuspended in water. Results were comparable. Once washed, cells were kept in an ice bath. It was also found that cells could be frozen and, when thawed, they responded normally to toxic chemicals in this assay.

Assays were performed by combining 1 ml Tris HCl buffer (0.1M, at pH 7.5), 1.2 ml of the toxic chemical, and 1 ml cells in 11×110 mm test tubes. Varying volumes of the toxic chemical were used at different times to get different concentrations of the chemical. For example, the toxic chemical and water were combined to a volume of 1.2 ml. Alternatively, toxic chemicals were made up as 3300 mg/l solutions so the volume of toxic chemical causing 50% reduction in absorbency was equal to the concentration of the chemical.

The absorbance was measured at the optimum wave length for the dye being used. In experiments with the method of the invention, six tetrazolium dyes were tested including: TTC, 2,3,5-triphenyltetrazolium chloride; TV, tetrazolium violet (2,5-diphenyl-3-(α-napthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-|3,3'-dimethoxy(1, 1'-biphenyl)-4,4'-diyl|-bis(2,5-diphenyl-2H-tetrazolium) dichloride); MTT (3-|4,5-dimethylthiazol-2-yl|-2,5-diphenyltetrazolium bromide); and NBT, Nitro blue tetrazolium (2,2'-di-nitrophenyl-5,5'-diphenyl-3,3'(-3,3'-dimethoxy-4,4'-diphenylene)ditetrazolium chloride). Also tested were a resazurin dye system and DCIP (2,6-dichlorophenol-indophenol). These dyes are readily available in the commercial market. In this description of a preferred embodiment, tetrazolium dye is being used as a representative example.

The time=0 absorbance was measured. Following the time=0 measurement, typically 0.1 ml of a 2.3 mM tetrazolium dye was added to a final volume of 3.3 ml, although any suitable volume may be used.

After each addition, the tubes were mixed vigorously with a vortex mixer. Tubes were then incubated at 30° C. in a stationary water bath. Results are much lower if the tubes are shaken during the assay. After 20 minutes to several hours, depending on the tetrazolium dye used, the absorbance was read again. The time=0 absorbance was subtracted from the final absorbance. The difference between the time=0 and the final absorbance was the "absorbance" used in calculations. Absorbance was read using a 30-year-old Bausch and Lomb Spectronic 20.

The data were plotted with the concentration or the volume of the toxic chemical on the X-axis and the absorbance on the Y-axis. Regression lines were calculated usually with a hand calculator, and the slope of the line, the Y intercept, and the regression coefficient were determined. Regardless of the shape of the curve, a linear regression was fitted to the data obtained. The calculation, X=(Y/2-B)/m, was solved to determine the concentration of toxic chemical resulting in 50% inhibition of reduction of the dye as estimated from the absorbance of the culture, also referred to as the IC50 (inhibitory concentration, 50%).

With some chemicals, a linear plot did not provide good data. The absorbance was plotted versus the log of the concentration of the toxic chemicals to obtain satisfactory results. Using the calculation, log X=(Y/2−B)/m, the antilog of log X is the concentration of chemical resulting in a 50% decrease in the absorbance. In most determinations, values were comparable using either a linear plot or the log plot. The data was analyzed and evaluated using a pocket calculator (Hewlett Packard 32SII). Values can also be plotted and the regression line calculated on a computer with commercially available software, e.g., an Apple Computer using Cricket Graphics.

If the regression coefficient, $r^2$, value for the data was less than 0.80, the data were not used. In the experiments and data shown herein, the assays were repeated with at least three batches of cells before the values obtained were considered representative. In the laboratory, the data was plotted using a computer, and values that were not in the linear portion were dropped, e.g., the last three points on the curve for pentachlorophenol (see FIG. 5). Using a pocket calculator, the last value was simply dropped until the regression coefficient stopped changing.

The data reported in the tables was calculated from the data with a satisfactory value for the regression coefficient. The mean and standard deviation were calculated, and the values greater or less than the standard deviation were discarded as "outliers". Typically, no more than 3 points were discarded. The mean and standard deviation were again calculated.

The following examples are given as illustrations of the present invention. In the Tables provided for the following examples, "n" refers to the number of values included in this mean (i.e., the number of samples used to calculate the toxic value). "ppm or average (ppm)" refers to the average value calculated from the samples included in the calculations (i.e., the equivalent toxic dose), expressed as parts per million (mg $l^{-1}$), and the CV, coefficient of variance, is the standard deviation divided by the mean for the sample, multiplied by 100, and reported as a percentage of the mean.

EXAMPLE 1

Choice of Bacteria and Dye

Table 1 below presents the results of the experiments with the various bacteria and dyes.

TABLE 1

| Bacterium | incubation time (hrs.) | MTT | INT | TB | TTC | NBT | TV |
|---|---|---|---|---|---|---|---|
| R. meliloti | 2:00 | 0.96 | 0.48 | 0.12 | 0.09 | 0.16 | 0.08 |
| R. leguminosarum | 7:48 | 0.04 | 0.02 | 0 | 0 | 0 | 0 |
| B. japonicum | 7:48 | 0.42 | 0.44 | 0.02 | 0.07 | 0.01 | 0.14 |
| Ps fluorescens | 1:57 | 0.3 | 0.17 | 0.05 | 0.01 | 0.04 | 0.01 |
| A. crystallopoites | 2:00 | 0.14 | 0.14 | 0.22 | 0.09 | 0.27 | 0.08 |
| S. typhimurium | 2:00 | 0.27 | 0.06 | 0.22 | 0.04 | 0.24 | 0.04 |
| E. coli | 1:40 | 0.58 | 0.12 | 0.04 | 0.14 | 0.1 | 0.03 |
| S. lactis | 9:57 | 0.09 | 0.08 | 0.04 | 0.05 | 0.06 | 0.04 |
| B. megaterium | 2:00 | 0.18 | 0.16 | 0.17 | 0.1 | 0.19 | 0.07 |
| R. sphaeroides | 11:25 | 0.45 | 0.95 | — | 0.12 | 0.16 | 0.12 |

Cells were grown in a variety of media, harvested, washed once with 0.01M phosphate buffer (pH 7.5), and the A550 was adjusted to 0.3. After the absorbance reading, 1 ml of the cells, 1 ml Tris buffer (0.1M, pH 8.0), 1.2 ml water and 0.1 ml of a 2.4 mM solution of each dye were combined. Cells were incubated at 30° C. for the time indicated in hours.

For some samples, e.g., lead, precipitates formed. The assay was tried with cells resuspended in water and without the addition of buffer to reduce the ions that could contribute to the precipitate. The results were comparable with the routine method, with cells in 0.01M phosphate buffer, pH 7.5 and with 0.1M Tris buffer, pH 7.5.

Of the ten bacteria tested, R. meliloti was found to give the greatest change in the optical absorbance in the shortest time. An absorbance of 0.4–0.8 was reached with 20 minutes of incubation. More specifically, R. meliloti with MTT dye gave A550=0.65–0.70 after a 20 minute incubation.

Several strains of R. meliloti were investigated. Strain 102f34 gave the best results. Preliminary evidence indicates that any strain of this non-pathogenic bacterium works well.

Figure 1:
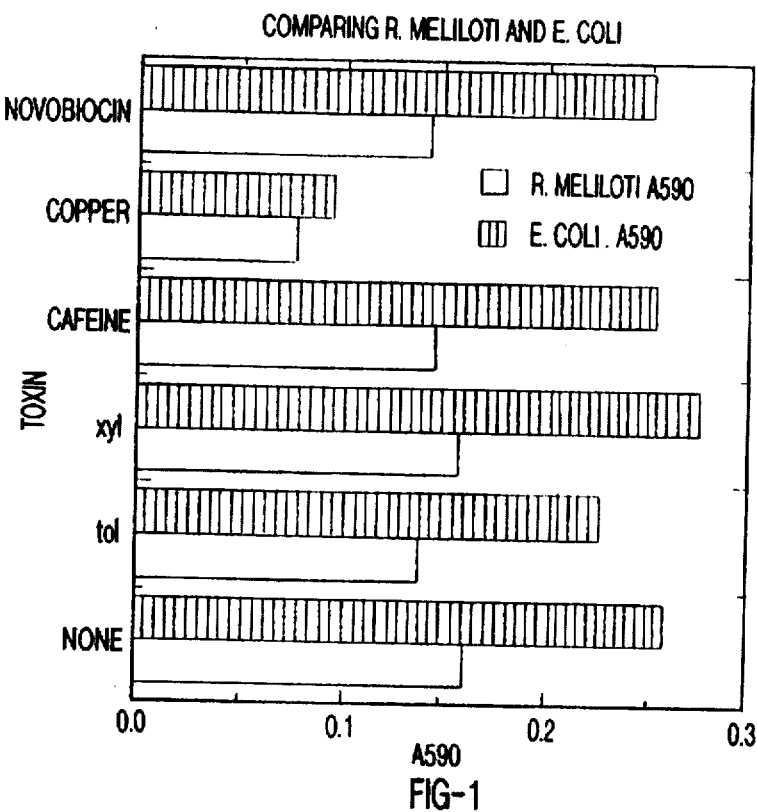
FIG. 1 is a graph showing data comparing the absorbance of the bacteria *R. meliloti* and *E. coli* at A590 for different toxins.

The other strains of bacteria, mixed in a buffer with various toxic chemicals, which were tested with the tetrazolium dye, gave varying results. Some bacteria reduced the dye, but the reduction was not inhibited appreciably by toxic chemicals. The absorbance of tetrazolium by Rhodobacter sphaeroides was not inhibited by copper. E. coli reduced the dye, but reduction was not inhibited by xylene. Results were comparable in E. coli when it was grown in LB aerobically (with shaking), or anaerobically (in stoppered flasks, stationary), or when cells were grown aerobically in minimal M63 medium with succinate or glucose. The other bacteria did not provide rapid reduction of the dye. S. lactis which has no respiratory activity did not reduce any of the dyes. FIG. 1 is a graph showing data comparing the absorbance of the bacteria R. meliloti and E. coli at A590 varying between 0.0 and 0.3 in reacting with different toxins.

The six dyes tested were obtained from Sigma Chemicals and were used as received. Of the dyes tested, MTT was found to be reduced most rapidly by R. meliloti. Of the other five additional tetrazolium dyes tested, including triphenyl tetrazolium chloride, tetrazolium violet, tetrazolium blue, iodonitrotetrazolium and nitro blue tetrazolium. Iodonitrotetrazolium (INT) worked well, but the reduction is not as rapid as with MTT. Tetrazolium violet (TV) worked well, but it also reduced more slowly than MTT, and the samples had to be incubated overnight to get big enough changes in the absorbance to test effectively.

The assay of the invention was run using 2,6-dichlorophenol-indophenol (DCIP) and resazurin, and neither of these dyes worked well for this example. Resazurin reduction by E. coli used to assay for toxic chemicals with the protocol used with the tetrazolium dyes did not yield useful results for this example. DCIP, another dye that is used to assay for reductase, was reduced very slowly by R. meliloti, and further experiments were abandoned.

All of these dyes were tested with 0.1 ml at 2.5 mM concentration, and a final concentration of 936 µM. Incubations were continued until the absorbance of the dye stopped increasing.

Figure 2:
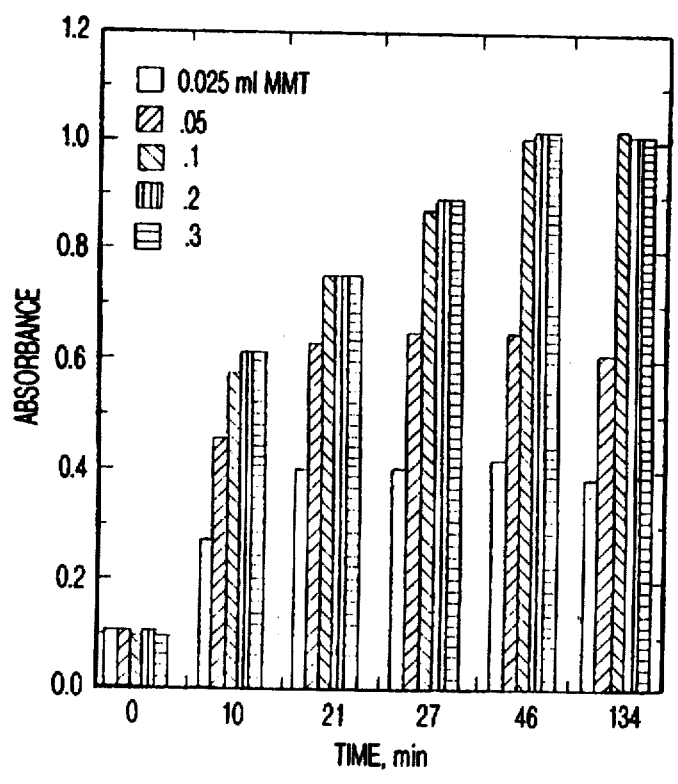
FIG. 2 is a graph showing data for absorbance of MTT dye at various concentrations versus time measured from 0 to 134 minutes.

FIG. 2 presents representative data for absorbance (from 0.0 to 1.2 absorbance units) of dye at various concentrations (from 0.025 to 0.3 ml of MTT dye) versus time measured from 0 to 134 minutes. The data shown in FIG. 2 led to some of the parameters of this preferred embodiment of the invention: the choice of 0.1 ml MTT dye and a 20-minute incubation time. Typically, the reduction of the dye increases at a linear rate for about 10 minutes, then slows.

In several experiments, cells were incubated for longer periods. Very little difference in the results was observed. Eventually the absorbance stopped increasing, and 1.0 seemed to be the maximum absorbance observed. The absorbance in samples with toxic chemicals increased, but not out of proportion to the increase in the controls. The inhibited samples did not eventually "catch up" to the controls. With some toxic chemicals at higher concentrations, the absorbance indicative of reduction of the tetrazolium did not change after the initial 20-minute sampling.

EXAMPLE 2

Growth of Cells

For growing cells, cultures were typically inoculated with a 1% inoculum of cells. It was found that the age of the inoculum affected the ability of the cells to reduce the dye. Cultures from old inocula, even after 5–6 generations, were found to be impaired in their ability to reduce the dye. Also, these cultures did not sediment as well. Apparently, the age of the inoculum affects the activity of the subsequent population of cells.

Preferably, the inoculum should be 30–36 hours old and grown in the same medium. Most preferably, a 1% inoculum is used and the cells are grown overnight.

Results of experiments are shown in Table 2, which provides data showing the effect of inoculum age on ability of cells to reduce MTT. "Reduction" refers to the reduction of tetrazolium dye.

TABLE 2

| A550 | Inoculum | | |
|---|---|---|---|
| | 4 wks. old | 5 days old | 36 hrs. old |
| initial | 0.03 | 0.03 | 0.01 |
| 16 hours | 0.19 | 0.68 | 0.50 |
| 20 hours | 0.52 | 1.04 | 0.85 |
| after washing | 0.28 | 0.94 | 0.75 |
| Reduction | 0.173 | 0.403 | 0.46 |

The age of the culture does not seem to affect the results. Cells may be harvested with the absorbance 550 nm ranging from 0.6 (exponential growth) to 2.3 (stationary growth). Little difference in the results were observed. Typically, 25 to 50 ml cells were grown, and typically, the bacteria are grown in a simple defined medium supplemented with casamino acids (milk protein).

EXAMPLE 3

The Electron Transport Mechanism

In the assay of the invention, the dyes appear to be reduced by electron transport. Most toxic chemicals affect membrane integrity, which in turn affects electron transport. Presumably, the dyes compete with oxygen or with other components in the electron transport system of the cell for electrons. The compounds that appear to be toxic are organic compounds known to affect membrane integrity or metal ions that could compete with the iron found in cytochromes in electron transport.

In experiments using the assay of the invention, reduction of MTT was obtained in three different aerobic conditions; the reactions were run to limit oxygen exchange with the cells. "Routine" treatments were performed as all the assay experiments were normally done, with samples in a final volume of 3.3 ml in a 13×110 mm test tube (uncapped), and tubes vortexed vigorously after each addition. "Anaerobic" treatments used samples in a final volume of 3.3 ml in 13×110 mm test tube. Cells were added to the tube, absorbency was measured (time=0), and dye was added. The tube was capped with parafilm and contents were mixed by inversion one time. "Aerobic" treatments used samples mixed in test tubes, and then added to 25 ml Erlenmeyer flasks and incubated on a rotary shaker incubator. All samples were incubated 20 minutes at 30° C. In Table 3, the results of this experiment are depicted.

TABLE 3

| Treatment | Absorbance |
|---|---|
| "Routine" | 0.32 |
| "anaerobic" | 0.32 |
| "aerobic" | 0.12 |

Incubating the samples in Erlenmeyer flasks with shaking obviously inhibits reduction of the dye. Therefore, the data presented in Table 3 show generally that reduction of the dye is inhibited when samples are aerated and support the theory that, in the assay of the invention, the dyes are reduced by electron transport and compete with oxygen for electrons in the respiratory chain.

Also, this assay did not work with bacteria lacking an electron transport mechanism. When S. lactis was tested for its ability to reduce the dyes, none of the dyes were reduced appreciably. It is known that this bacterium totally lacks a respiratory system. The failure of this bacterium to reduce the dyes supports the hypothesis that the dyes are reduced by electron transport.

FCCP is known to inhibit tetrazolium reduction at a much lower concentration than does DNP. Also, these compounds are known to uncouple respiration, electron transport, and phosphorylation from ATP synthesis to prevent formation of ATP. In mitochondria, these compounds stimulate oxygen uptake and increase the rate of electron transport, i.e., oxygen consumption is stimulated by these compounds indicating that electron transport is stimulated when it is uncoupled from ATP synthesis (C. K. Mathews and K. E. van Holde, Biochemistry, p. 524 (1990)). Therefore, it would have been anticipated that these compounds would stimulate reduction of the dye rather than inhibit.

It was also found, during experiments with this assay, that washing cells in buffer containing 10 mM EDTA precluded reduction of the dye. It is known that EDTA removes divalent cations from the cytoplasmic membrane and alters the structure of the cytoplasmic membrane. Presumably, this disrupts electron transport sufficiently to preclude reduction of the dye.

The exact mechanism for reduction of the dye is uncertain. The dye precipitates on the surface of the cells. After the reaction, cells could be centrifuged out of suspension, and the reduced blue dye would be concentrated with the cells. When the cells were resuspended, the dye would also be resuspended. The cells could not be separated from the reduced dye. Tetrazolium salts have been used in methods to visualize live cells in situ. These methods take advantage of the precipitation of the dye when it is reduced, which fixes the dye to the cell. Cytochrome C is thought to be on the outer surface of the cytoplasmic membrane. Tetrazolium dyes may be reduced by cytochrome C; similarly, methane and hydrogen are known to be oxidized in the periplasm by cytochrome C. Alternatively, tetrazolium dyes could be reduced by a non-specific reductase on the outer surface of the cytoplasmic membrane.

EXAMPLE 4

Inhibition of Tetrazolium Reduction by Organic Compounds

In experiments with organic compounds using the method of the present invention, the effect of toxic compounds on the inhibition of tetrazolium dye reduction due to the inhibition of electron transport was investigated, as either a direct effect (the compounds compete with tetrazolium for critical sites in the system), or an indirect effect (the compounds alter the cytoplasmic membrane, thus inhibiting electron transport).

FIGS. 3, 4, and 5 are representative graphs of typical data for these experiments, showing the absorbance of the compounds dinitrophenol (DNP), saccharin, and pentachlorophenol (PCP), respectively. These Figures plot the A550 value (absorbance at 550 nm) as a function of the concentration of the chemicals in ppm.

All three compounds inhibited tetrazolium reduction; however, different compounds gave different curves, indicating that no two toxic chemicals give quite the same response. In FIG. 3, DNP gave a hyperbolic curve. With saccharin (FIG. 4), the inhibition was linear with respect to the concentration of the toxic agent; as shown on the graph, the IC50 value was determined to be 477 ppm. As with some other compounds, the PCP (FIG. 5) inhibition was logarithmic, i.e. the inhibition increased with the log of the concentration of the toxic chemical. The PCP curve was very steep initially, then the decrease became less dramatic; the IC50 value for PCP was calculated from the first 5 points on this graph. These differences suggest there may be more than one mechanism to account for the inhibition of reduction of the dye.

Also, with DNP (FIG. 3), the reduction stopped when the absorbance was 0.2, and FIG. 5 shows that the log PNP did not reduce more than 0.25. However, in FIG. 4, the linear saccharin curve shows that, for saccharin, the reduction would eventually go to 0.0. It was found that increasing the amount of the inhibitory agent in cases where the reduction of the dye does not go to 0, does not increase inhibition.

Representative results for tests with miscellaneous organic compounds are presented in Table 4, below. In this Table, FCCP is carbonyl-cyanide p(triflouromethoxy) phenylhydrozone, an inhibitor of electron transport.

TABLE 4

| Compound | n | average (ppm) | CV |
|---|---|---|---|
| Dinitrophenol | 5 | 574 | 36% |
| FCCP | 6 | 0.114 | 35% |
| Trichlorophenol | 7 | 3..95 | 33% |
| Pentachlorophenol | 9 | 0.206 | 52% |
| Sodium lauryl sulfate | 3 | 30.4 | 9% |
| Chloroform | 3 | 2032 | 5% |
| Phenol | 4 | 1316 | 13% |
| Carbon tetrachloride | 5 | 3530 | 11% |
| trichloroethylene | 8 | 59.5 | 18% |
| tetrachloroethylene | 5 | 34.8 | 17% |

Trichlorophenol and pentachlorophenol are both noted environmental pollutants, and both inhibit reduction of tetrazolium dye; however, inhibition by pentachlorophenol is an order of magnitude greater than the inhibition by trichlorophenol.

Sodium lauryl sulfate, a detergent, inhibits reduction of tetrazolium dye by solubilizing critical components of the electron transport system and uncoupling the system.

Chloroform, carbon tetrachloride and phenol interact with the phospholipids in the cytoplasmic membrane and uncouple electron transport. However, relatively high concentrations of these compounds are required for the effect. Solid phenol was dissolved in water and added to the reaction tubes. Chloroform and carbon tetrachloride were found to be very immiscible in water. In producing the results shown above, chloroform and carbon tetrachloride were assayed simply by the addition of these immiscible compounds in the test tubes.

Trichloroethylene and tetrachloroethylene are toxic chemicals used to wash airplanes. For the assay, both were dissolved in DMSO.

When a few μl of these compounds were added to the sample tubes and mixed vigorously, the compound collected at the bottom of the tube. A chloroform-saturated solution of water was prepared: 1 ml chloroform was added to 100 ml water in a separatory funnel. The funnel was shaken, the two layers allowed to form, then the chloroform was drained from the funnel. The Merck Index (Merck & Co., Inc. Rahway, N.J., (1968)) states that 1.476 gm (1 ml) is soluble in 200 ml water, equivalent to 7.38 mg/ml. In assaying this chemical according to the method of the invention, it was found that the IC50 for this solution of chloroform was 827 μl (n=6). This is 6.10 mg/tube or 1.85 mg/ml (3.3 ml in each tube), or 1850 ppm. Assaying the effect of chloroform directly, by simply adding it to the reaction tubes, yielded an IC50 of 4132 ppm.

The same approach was used with carbon tetrachloride. However, it was impossible to obtain inhibitory data over a wide enough range of volumes of the saturated solution to provide useful data. Carbon tetrachloride measured directly, by simply adding it to the reaction tubes, gave an IC50 of 3530 ppm.

Calcium is also toxic at a level of 6 ppm, which in the absence of a counteracting substance would preclude testing of calcareous soil and water bodies with high calcium levels (such as the Rio Grande). If 500 μl of 5 mM EDTA is added to the reaction (0.758 mM EDTA), calcium at 19 ppm does not affect the reaction. The addition of EDTA eliminates the inhibition of reduction by calcium and stimulates the reduction slightly. This permits calcareous water and soil samples to be assayed for toxic chemicals.

EXAMPLE 5

Benzene, Toluene, and Xylene

Benzene, toluene and xylene are considered to be indicative of pollution by petroleum. Like chloroform, carbon tetrachloride and phenol, these chlorinated aromatic compounds interact with the phospholipid component of the cytoplasmic membranes and uncouple electron transport, thus inhibiting it.

The results as to toxicity of assays of these compounds using three different techniques, are shown in Table 5 below.

TABLE 5

| Method | Benzene | | | Toluene | | | Xylene | | |
|---|---|---|---|---|---|---|---|---|---|
| | n | ppm | CV | n | ppm | CV | n | ppm | CV |
| direct | 17 | 2584 | 28% | 15 | 661 | 24% | 12 | 476 | 43% |
| QSAR | 1 | 1020 | | 1 | 230 | | 1 | 30.3 | |
| 10,000 ppm/ml | 3 | 730 | 8.3% | 3 | 317 | 28% | 3 | 151 | 41% |

In the "direct" method, the hydrocarbon was simply added to the test tube, and the cells were added. The tube was mixed very vigorously with the vortex mixer. This method was the least sensitive.

In the second method, QSAR, the hydrocarbons were added to water, mixed vigorously, and the aqueous phase separated from the hydrocarbon with the separatory funnel. The aqueous phase was assayed for toxicity. The amount of hydrocarbon in the water was determined from data obtained by the QSAR method, which is essentially a mathematical model to estimate the solubility of chemicals in water.

A third approach was to simply calculate the volume of the hydrocarbon providing 10,000 ppm (10,000 mg/l), and to add this volume using a Hamilton syringe. This 10,000 ppm stock was assayed for the volume causing 50% inhibition of reduction.

These three methods resulted in significantly different values for the toxicity of the three hydrocarbons; however, with these three methods, benzene was least toxic and xylene was the most toxic. In comparison, using the Poly-tox™ method described above, Sun, B., *Comparison of Inter Species Toxicity of Organic Chemicals and Evaluation of QSAR Approaches in Toxicity Prediction*, M. S. Thesis, Environmental Engineering, New Mexico State University (1993), obtained values of 685 ppm, 207 ppm and 140 ppm for benzene, toluene, and xylene respectively.

Comparatively, the assay of the current invention is not as sensitive as some of the other tests to benzene, toluene, and xylene directly, however, it is still effective, and simpler. FIGS. 6, 7, and 8 offer representative plots of typical data for experiments using the assay of the invention for testing toluene, xylene, and water saturated with all three aromatics, respectively. In FIG. 6, absorbance at 550 nm is plotted as a function of toluene concentration in ppm; in FIGS. 7 and 8 absorbance at 550 nm is plotted as a function of volume of the chemicals in μl.

Waste motor oil is another petroleum product that is a significant problem in the environment. There is concern that toxic chemicals can be washed from the waste motor oil and contaminate ground water. Toxic petroleum compounds in waste motor oil were directly tested using the assay of the present invention. From samples of used motor oil, which had been used for about 3,000 miles in a new automobile burning unleaded gasoline, 1 ml motor oil was combined with 9 ml water in a test tube. The tube was shaken very vigorously with the vortex mixer. Several samples were heated in the microwave oven to a temperature of about 70° C. Using the assay of the present invention, these samples provided a mean IC50 volume of 272.5 μl (n=4, CV=40%).

The dry weight of 2.5 ml of the aqueous phase from the oil sample was determined. This indicates the toxicity of the aqueous phase to be 0.259 ppm with respect to the dried material from the aqueous phase. Thus, the assay of the invention is very sensitive to toxic compounds present in water extracts of waste motor oil. The present invention is highly useful in following contamination from petroleum products.

EXAMPLE 6

Toxicity of Solvents

The toxicity of solvents often used to dissolve toxic compounds was determined; the results of using this assay to test for these toxicants are presented in Table 6, where the IC50 volume is the volume of toxic solvent that inhibits reduction of the tetrazolium dye by 50%.

TABLE 6

| Solvent  | n | CV    | IC50 Volume | ppm     |
|----------|---|-------|-------------|---------|
| DMSO     | 8 | 17.5% | 467 μl      | 156,000 |
| Acetone  | 9 | 10.3% | 300 μl      | 71,636  |
| Ethanol  | 6 | 18.0% | 341 μl      | 75,573  |
| Methanol | 6 | 9.6%  | 287 μl      | 76,514. |

DMSO (dimethyl sulfoxide) was found to be least toxic. FIG. 9 presents a representative plot of the data for the DMSO experiments using the assay of the invention. In FIG. 9, the absorbance at 550 nm is plotted against the volume in μl of DMSO. The IC50 value was found to be 203.3 μl/tube.

Acetone, ethanol, and methanol were comparably toxic. All of these solvents were found to have a toxicity of about 300 μl/sample. Any of these solvents can be used with high concentrations of toxic compounds. With the assay of the invention, it was also found that the contribution of the solvent to the toxicity of the compound was minimal: in one test, FCCP was dissolved in DMSO, and it was found that the IC50 for FCCP was only a few μl.

EXAMPLE 7

Toxic Minerals

In Table 7, results of experiments to determine the toxicity of metals are presented.

TABLE 7

| Mineral   | n  | ppm     | CV  |
|-----------|----|---------|-----|
| Cadmium   | 7  | 0.838   | 23% |
| Calcium   | 12 | 5.230   | 22% |
| Cobalt    | 7  | 11.200  | 56% |
| Copper    | 11 | 0.960   | 9%  |
| Magnesium | 5  | 59.900  | 32% |
| Mercury   | 12 | 0.0179  | 36% |
| Zinc      | 6  | 4.750   | 6%  |
| Manganese | 14 | 0.892   | 26% |
| Selenium  | 6  | 226.000 | 16% |

Calcium was found to be toxic: 5.23 ppm is 0.04712 mM calcium chloride. Typically, R. meliloti is grown in medium with 10–20 uM calcium. Magnesium sulfate, at 59.9 ppm, is 0.2435 mM. The medium MDM contains 0.6 mm Magnesium chloride; this is a concentration found in most defined media. In a series of comparative experiments, $MgCl_2$ was found to inhibit the growth of R. meliloti NSI 50% at a concentration of 26.9 mM. It is not certain why this concentration of magnesium appears to be toxic for the bacterium in this assay for toxic chemicals, yet does not inhibit growth of the bacterium in a medium. CDM, the medium used in the experiments with the assay of the invention, is 0.81 mM with respect to magnesium.

The other metals found to be toxic were cadmium, cobalt, copper, mercury, and zinc, which are usually thought to be toxic and are present in bacterial media in very low concentrations.

FIGS. 10, 11, and 12 are plots of the data obtained for the experiments using the inventive assay with copper, mercury and sodium chloride respectively. FIG. 10 is a graph of the absorbance plotted as a function of the copper concentration. The IC50 value was calculated from this plot using the first six points. Copper stimulates the reduction of the dye at very low concentrations; this has been observed with several toxic compounds.

FIG. 11 is a graph of the absorbance plotted as a function of the volume of the mercury. Mercury, along with some other compounds, inhibited tetrazolium reduction completely. After incubation, the absorbance is comparable to a time=0 absorbance.

FIG. 12 presents a graph of absorbance at 590 nm plotted as a function of the volume of a 10% NaCl solution (not shown in the Table above). The IC50 value was found to be 606.89 μl or 60.689 ppm. The curve of the chemical went to 0.1 absorbance at 1000 μl of the solution.

Lead and iron (neither are shown in the Table above) were found to have no inhibitory effect on the reduction of tetrazolium dye by R. meliloti.

EXAMPLE 8

Comparative Testing

The results from experiments with the assay of the present invention have been compared with other assays using microbial and animal indicator organisms. The IC50 concentrations of toxic chemicals resulting in inhibition of 50% of the reduction of the tetrazolium dye have been determined for at least 17 organic compounds and 7 minerals. The values obtained for most of these compounds are comparable to the values obtained using other methods, both microbial and with animals. Some representative data are presented in Tables 8 and 9.

Table 8 presents the results of comparing the Rhizobium/Tetrazolium assay of the current invention with the previously described Microtox™ assay and an assay using fish (trout fingerlings) to provide comparable data with an animal test. Toxicity of compounds is given in parts per million (ppm) resulting in 50% inhibition (IC50) of the assay or 50% death of the fish (LD50). In this Table, the values for trichlorophenol and pentachlorophenol are from J. M. Ribo and K. L. E. Kaiser, *Chemosphere*, Vol. 12, pp. 1421–1442 (1983). The other values are from G. A. McFeters, P. J. Bono, S. B. Olson, and Y. T. Tohan, "A Comparison of Microbial Bioassays for the Detection of Aquatic Toxicants", *Water Resources* Vol. 17, pp. 1757–1762 (1983).

TABLE 8

|  | Microtox | Fish | Rhizobium/Tetrazolium |
|---|---|---|---|
| Mercury | 0.04–0.06 | 0.01–.9 | 0.0179 |
| Zinc | 476 | 0.24–7.20 | 4.75 |
| Copper | 24.96 | 0.1–10.7 | 0.240 |
| Cadmium | 416 | 1.0–100 | 0.210 |
| Phenol | 39.5 | 50–100 | 1223 |
| Benzene | 4.11 | 10–100 | 712 |
| Toluene | 33,833 | 23 | 590 |
| Trichlorophenol | 2.05–2.10 | — | 3.35 |
| Pentachlorophenol | 2.46–2.71 | — | 0.143 |

The results of the assay of the invention using *R. meliloti* cells and tetrazolium dye compare well with the results from both the Microtox™ assay and the toxicity studies using fish.

Additional values from other experiments for various toxic chemicals measured by the assay of the invention and the Microtox™ assay are presented in comparison in Table 9. Bitton, G. and Dutka, B. J., *Toxicity Testing Using Microorganisms*, CRC Press, Boca Raton, Fla. (1986); Green, J. C., et al., "A Comparison of 3 Microbial Assay Procedures for Measuring Toxicity of Chemical Residues", *Arch. Environ. Contam. and Toxicol.*, Vol. 14, pp. 569–667; Ribo, J. M. and Kaiser, K. L. E., "Effects of Isolated Chemicals to Photoluminescent Bacteria and Their Correlating with Acute and Sublethal Effects on Other Organisms", *Chemosphere*, Vol. 12, pp. 1421–1442 (1983); and Smith, S. N., and Pugh, G. J. F., "Evaluation of Dehydrogenase as a Suitable Indicator of Soil Microflora", *Enz. Microb. Tech.*, Vol 1, p. 279 (1979).

TABLE 9

| Compound | Microtox ppm | Rhizobium/Tetrazolium* ppm |
|---|---|---|
| Methanol | 11,368–320400 | 68,410 |
| Ethanol | 23,090–55,388 | 75,573 |
| Acetone | 13305–29,109 | 1,636 |
| DMSO | 3,506–102,995 | 174,456 |
| Cadmium | 416 | 0.210 |
| Copper | 4.9, 7.4, 3.5, 1.2 | .240 |
| Mercury | 0.06, .04–.08, 0.06 | .0179 |
| Zinc | 476, 2.5–49, 12 | 4.75 |
| Nickel | 34 | 49.3 |
| Phenol | 623 | 1,223 |
| Benzene | 410–201, 4.11 | 712–2100 |
| Toluene | 18.0–33,833 | 30–502 |
| Xylene | .70–9.25 | 146–452 |
| sodium dodecyl sulfate | 34, 1.19 | 31.0 |
| Trichlorophenol | 2.05–2.25 | 3.35 |
| Pentachlorophenol | 2.46–2.71 | 0.143 |

When the ratio of the inhibitory concentration of a chemical with the Rhizobium/Tetrazolium assay was compared with the Microtox™ assay, the Microtox™ assay was found to be at least an order of magnitude more sensitive than the Rhizobium/Tetrazolium assay for phenol, benzene, toluene, xylene, and sodium dodecyl sulfate. The Rhizobium/Tetrazolium assay was found to be at least an order of magnitude more sensitive for 4 compounds (cadmium, copper, zinc, and pentachlorophenol). The sensitivity to other compounds between the two tests differed by less than an order of magnitude.

Results obtained with the assay of the present invention are comparable to the Microtox™ test in many respects. As an example, the test is not as sensitive for trichlorophenol as the Microtox™ test (about an order of magnitude less sensitive); however, the test is two orders of magnitude more sensitive for pentachlorophenol. These two compounds are frequent contaminants in areas where wood is treated.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art, and it is intended to cover in the appended claims all such modifications and equivalents. The entire disclosures of all references, applications, patents, and publications cited above, are hereby incorporated by reference.

What is claimed is:

1. A method of testing for toxicants in a substance comprising the steps of:
    (a) adding a cell to the substance to form a mixture, wherein the cell is selected from the group consisting of plants; fungi; animals; and bacterial cells selected from the group consisting of *Bradyrhyzobium japonicum*, *Arthrobacter crystallopoites*, *Rhizobium meliloti*, *Rhizobium leguminosarum*, *Streptococcus lactis*, and *Rhodorseudonomas sphaeroides;*
    (b) adding to the mixture a dye which undergoes chemical reduction in the presence of the cell; and
    (c) quantitatively measuring inhibition of electron transport in the cell as a function of toxicants in the mixture.

2. The method of claim 1 wherein the toxicants comprise at least one member selected from the group consisting of chemicals, compounds, toxic substances, minerals, and mixtures thereof.

3. The method of claim 1 wherein the toxicants comprise at least one member selected from the group consisting of hydrocarbons, solvents, metals, and salts.

4. The method of claim 1, wherein the dye changes color during reduction, and the quantitative measuring step further comprises the step of monitoring the color change produced by reduction.

5. The method of claim 4, wherein the quantitative measuring step further comprises the steps of:
    measuring absorbance of the dye into the cell during chemical reduction; and
    calculating the concentration of toxicants in the mixture from absorbance data obtained in the measuring step.

6. The method of claim 5, wherein the step of measuring absorbance is performed at a wavelength chosen from the dye being used.

7. The method of claim 5, wherein the step of measuring absorbance is performed at a wavelength of 550 nm.

8. The method of claim 5, wherein the step of measuring absorbance is performed at a wavelength of 590 nm.

9. The method of claim 5, wherein the step of measuring absorbance is performed using a spectrophotometer.

10. The method of claim 1, wherein the dye is selected from the group consisting of TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxy(1,1'-biphenyl)-4,4'-diyl]-bis(2,5-diphenyl-2H-tetrazolium)dichloride); MTT (3-[4,5-dimethylthiazol-2-yl]-2,5-diphenyl tetrazolium bromide); and NBT, Nitro blue tetrazolium (2,2'-di-nitrophenyl-5,5'-diphenyl-3,3'-(3,3'-dimethoxy-4,4'-diphenylene) ditetrazolium chloride).

11. The method of claim 10, wherein the dye is TB.

12. The method of claim 1, wherein the step of adding a cell to the substance being tested further comprises the steps of growing the cell by inoculating a culture with an inoculum of cells and harvesting the cell.

13. The method of claim 12, wherein the cell is grown in a medium supplemented with an amino acid.

14. The method of claim 12, wherein the inoculum is not more than 36 hours old.

15. The method of claim 1 wherein the cell is washed.

16. The method of claim 1 wherein the cell is unwashed.

17. The method of claim 1 conducted in a solution.

18. The method of claim 17 wherein the solution comprises water.

19. The method of claim 17 wherein the solution comprises a buffer.

20. The method of claim 1 conducted in an aerobic environment.

21. The method of claim 1 conducted in an anaerobic environment.

22. The method of claim 1 further comprising the step of incubating the mixture for a sufficient time to substantially complete reduction.

23. A method of testing for toxicants in a substance comprising the steps of:
(a) adding a cell to the substance to form a mixture, wherein the cell is selected from the group consisting of plants; fungi; animals; and bacterial cells selected from the group consisting of *Bradyrhyzobium japonicum*, *Arthrobacter crystallopoites*, *Rhizobium meliloti*, *Rhizobium leguminosarum*, *Streptococcus lactis*, and *Rhodopseudonomas sphaeroides*;
(b) adding to the mixture a dye which undergoes chemical reduction in the presence of the cell and changes color;
(c) incubating the mixture during reduction of the dye;
(d) quantitatively measuring a change in color intensity of the dye during the incubating step, the change being indicative of the inhibition of electron transport and the decrease in reduction of the dye over time; and
(e) calculating the concentration of toxicants in the mixture from data obtained in the measuring step.

24. The method of claim 23, wherein the dye is selected from the group consisting of TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxy(1,1'-biphenyl)-4,4'-diyl]-bis(2,5-diphenyl-2H-tetrazolium)dichloride); MTT (3-[4,5-dimethylthiazol-2-yl]-2,5-diphenyltetrazolium bromide); and NBT, Nitro blue tetrazolium (2,2'-di-nitrophenyl-5,5'-diphenyl-3,3'-(3,3'-dimethoxy-4,4'-diphenylene) ditetrazolium chloride).

25. The method of claim 24, wherein the dye is TB.

26. The method of claim 23, wherein the step of adding a cell to the substance further comprises the step of suspending the mixture in buffer.

27. The method of claim 23, wherein the incubating step is performed in minutes.

28. The method of claim 23, wherein the incubating step further comprises heating the mixture.

29. The method of claim 23, wherein the step of quantitatively measuring further comprises the steps of:
measuring a first absorbance of the dye into the cell at time=0;
sequentially measuring absorbance of the dye during the incubation step;
subtracting the first absorbance from a final absorbance determined by an end point of absorbance established from the sequential measuring step;
obtaining from the subtracting step a total absorbance to be used in the calculating step; and
plotting the total absorbance on a Y axis against the toxicants in the substance being tested on an X axis.

30. The method of claim 29, wherein the plotting step further comprises plotting the total absorbance against a concentration of the toxicants in the substance being tested.

31. The method of claim 29, wherein the plotting step further comprises plotting the total absorbance against a volume of the toxicants in the substance being tested.

32. The method of claim 23, wherein the calculating step further comprises the steps of:
plotting the data against the toxicants in the substance being tested;
calculating and fitting a regression line to the data;
determining a slope, a Y-intercept, and a regression coefficient from the regression line;
establishing the toxicity of the toxicants by calculating a concentration of toxicants resulting in a percentage decrease in reduction of the dye, from the slope and the Y-intercept of the regression line, using an equation, $Y/2=mX+B$, where Y equals the absorbance of a control sample without a toxicant, m is the slope of the regression line, B equals the Y-intercept, and X equals the concentration of toxicants; and
expressing the concentration to quantitate the toxicity of the toxicants.

33. The method of claim 32, wherein the plotting step further comprises plotting the data against a concentration of toxicants in the substance being tested, and the calculating step further comprises solving the equation for $$X = \frac{Y/2 - B}{m}.$$

34. The method of claim 32, wherein the plotting step further comprises plotting the data against a volume of toxicants in the substance being tested, and the calculating step further comprises solving the equation for $$\log X = \frac{Y/2 - B}{m}$$

and calculating the antilog of log X to determine the concentration of toxicant.

35. A method of testing for the presence of toxicants in a substance comprising:
(a) adding a cell having a cytoplasmic membrane to the substance being tested to form a mixture, wherein the cell is selected from the group consisting of plants; fungi; animals; and bacterial cells selected from the group consisting of *Bradyrhyzobium japonicum, Arthrobacter crystallopoites, Rhizobium meliloti, Rhizobium leguminosarum, Streptococcus lactis,* and *Rhodopseudonomas sphaeroides;*

(b) suspending the mixture;

(c) measuring absorbance in the mixture at an appropriate wavelength at time=0;

(d) adding to the mixture a dye capable of chemically reducing and changing color in the presence of the cell;

(e) incubating the mixture, thereby causing reduction of, and a resulting color change in, the dye;

(f) measuring absorbance of the dye in the cell membrane during the incubating step, the absorbance decreasing over time from the time=0 absorbance to an endpoint absorbance equivalent to an endpoint of substantial reduction of the dye, as demonstrated by a change in color intensity of the dye over time;

(g) subtracting the time=0 absorbance from the endpoint absorbance to arrive at an absorbance difference;

(h) plotting the absorbance difference on a Y axis versus the toxicants on an X axis;

(i) calculating a regression line, and thereby determining a slope of the line, a Y intercept, and a regression coefficient;

(j) solving an equation Y/2=mX+B for an X value, where Y is the absorbance of a control sample without a toxic chemical, m is the slope, B is the Y intercept, and X is a concentration of toxicant causing a percentage decrease in reduction of the dye; and (k) calculating the x value to quantitate the toxicity of the toxicants in the substance being tested.

36. The method of claim 35, wherein the dye is selected from the group consisting of TTC, 2,3,5-triphenyltetrazolium chloride; TV, tetrazolium violet (2,5-diphenyl-3-(α-naphthyl)tetrazolium chloride); INT, p-iodo nitrotetrazolium violet (2-(4-iodophenyl)-3-(4-nitrophenyl)-5-phenyltetrazolium chloride; TB, tetrazolium blue chloride (3,3'-[3,3'-dimethoxy(1,1'-biphenyl)-4,4'-diyl]-bis(2,5-diphenyl-2H-tetrazolium)dichloride); MTT (3-[4,5-dimethylthiazol-2-yl]-2,5-diphenyltetrazolium bromide); and NBT, Nitro blue tetrazolium (2,2'-di-nitrophenyl-5,5'-diphenyl-3,3'-(3,3'-dimethoxy-4,4'-diphenylene)ditetrazolium chloride).

37. The method of claim 36, wherein the dye is TB.

* * * * *